(12) United States Patent
Lopez-Tapia et al.

(10) Patent No.: US 6,903,086 B2
(45) Date of Patent: Jun. 7, 2005

(54) ALKOXYCARBONYLAMINO BENZOIC ACID OR ALKOXYCARBONYLAMINO TETRAZOLYL PHENYL DERIVATIVES AS IP ANTAGONISTS

(75) Inventors: Francisco Javier Lopez-Tapia, Union City, CA (US); Dov Nitzan, San Jose, CA (US); Counde O'Yang, Sunnyvale, CA (US)

(73) Assignee: SYNTEX (U.S.A.) LLC, Palo Alto, CA (US)

( * ) Notice: Subject to any disclaimer, the term of this patent is extended or adjusted under 35 U.S.C. 154(b) by 142 days.

(21) Appl. No.: 10/087,034

(22) Filed: Mar. 1, 2002

(65) Prior Publication Data

US 2002/0165235 A1 Nov. 7, 2002

Related U.S. Application Data

(60) Provisional application No. 60/312,559, filed on Aug. 15, 2001, and provisional application No. 60/272,872, filed on Mar. 2, 2001.

(51) Int. Cl.$^7$ .................. A61K 31/33; A61K 31/34; C07D 257/04; C07D 209/00; C07D 307/00
(52) U.S. Cl. .................. 514/183; 514/381; 514/449; 514/467; 514/469; 549/432; 549/434; 549/462; 549/491; 549/497; 548/250; 548/252
(58) Field of Search .................. 514/183, 381, 514/449, 467, 469; 548/250, 252; 549/432, 434, 462, 491, 497

(56) References Cited

U.S. PATENT DOCUMENTS

| | | | |
|---|---|---|---|
| 5,998,424 A | 12/1999 | Galemmo, Jr. et al. | 514/269 |
| 6,174,905 B1 | 1/2001 | Suzuki et al. | 514/346 |
| 6,184,242 B1 | 2/2001 | Bley et al. | 514/407 |
| 2001/0056100 A1 | 12/2001 | Cournoyer et al. | 514/307 |

FOREIGN PATENT DOCUMENTS

| | | |
|---|---|---|
| EP | 0974576 A2 | 1/2000 |
| EP | 974576 * | 1/2000 |
| WO | WO 00/06550 A1 | 7/1998 |
| WO | WO 01/68591 A1 | 9/2001 |

OTHER PUBLICATIONS

Liu et al, PubMed Abstract 12447698, also cited as Oncogene, 21/54, 8347–50(2002).*
Ueno et al, PubMed Abstract 11338374, also cited as Nippon Yakurigaku Zasshi, 117/4, 255–61(2001).*
Kurashi et al, PubMed Abstract 11338373, also cited as Nippon Yakurigaku Zasshi, 117/4, 248–54(2001).*
Nishio et al, PubMed Abstract 2514128, also cited as Nippon Yakurigaku Zasshi, 94/6, 351–61(1989).*
Vapaatalo et al, PubMed Abstract 212650, also cited as Med. Biol., 56/4, 163–83(1978).*

Bley, et al., "The role of IP prostanoid receptors in inflammatory pain", *Trends in Pharmacological Sciences*, Apr. 1998, pp. 141–147,19 (4), Elsevier Science Ltd.
Smith, et al., "Characterization of prostanoid receptor-evoked responses in rat sensory neurons," *British Journal of Pharmacology*, 1998, pp. 513–523, 124(3), Stockton Press.
Murata, et al., "Altered pain perception and inflammatory response in mice lacking prostacyclin receptor," *Nature*, 1997, pp. 678–682, 388(6643), Macmillan Magazines Ltd.
Anderson, et al., "Pharmacology of Lower Urinary Tract Smooth Muscles and Penile Erectile Tissues," *Pharmacological Reviews*, 1993, pp. 253–308, 45(3).
Coleman, et al., "VIII. International Union of Pharmacology. Classification of Prostanoid Receptors: Properties, Distribution, and Structure of the Receptors and Their Subtypes", *Pharmacological Reviews*, 1994, pp. 205–229, 46(2).
Tsubaki, Kazunori, "A Novel Pyridazinone Derivative as a Nonprostanoid PGI$_2$ Agonist" *Pergamon, Bioorganic & Medicinal Chemistry Letters*, (2000), pp. 2787–2790, vol. 10.

* cited by examiner

*Primary Examiner*—Richard L. Raymond
*Assistant Examiner*—Sudhaker B. Patel
(74) *Attorney, Agent, or Firm*—Robert C. Hall

(57) ABSTRACT

This invention relates to compounds which are generally IP receptor antagonists and which are represented by Formula I:

wherein $G^1$ is selected from the group consisting of a, $b^1$ and $b^2$, and A and $G^2$ are as defined in the specification; or pharmaceutically acceptable salts or solvates thereof. The invention further relates to pharmaceutical compositions containing such compounds, methods for their use as therapeutic agents, and methods of preparation thereof.

20 Claims, No Drawings

ALKOXYCARBONYLAMINO BENZOIC ACID OR ALKOXYCARBONYLAMINO TETRAZOLYL PHENYL DERIVATIVES AS IP ANTAGONISTS

CROSS REFERENCE TO RELATED INVENTIONS

This application claims benefit under Title 35 U.S.C. 119(e) of U.S. Provisional Applications Nos. 60/272,872 filed Mar. 2, 2001, and No. 60/312,559 filed Aug. 15, 2001, all applications are hereby incorporated by reference in its entirety.

FIELD OF THE INVENTION

This invention relates to certain alkoxycarbonylamino benzoic acid derivatives and alkoxycarbonylamino tetrazolyl phenyl derivatives, and associated pharmaceutical compositions, methods for use as prostaglandin IP ($I_2$, or $PGI_2$) antagonists, and methods of preparation thereof.

BACKGROUND OF THE INVENTION

Prostaglandins or prostanoids (PGs) are a group of bioactive compounds derived from membrane phospholipids and are formed from 20-carbon essential fatty acids containing three, four, or five double bonds, and a cyclopentane ring. They fall into several main classes designated by the letters D, E, F, G, H, or I, and they are distinguished by substitutions to the cyclopentane ring. The main classes are further subdivided by subscripts 1, 2, or 3, which reflect their fatty acid precursors. Thus, $PGI_2$ has a double ring structure, and the subscript 2 indicates that it is related to arachidonic acid.

Prostaglandins are known to be generated locally in the bladder in response to physiologic stimuli such as stretch of the detrusor smooth muscle, injuries of the vesical mucosa, and nerve stimulation (K. Anderson, *Pharmacological Reviews* 1993, 45(3), 253–308). $PGI_2$ (also known as prostacyclin) is the major prostaglandin released from the human bladder. There are some suggestions that prostaglandins may be the link between detrusor muscle stretch produced by bladder filling and activation of C-fiber afferents by bladder distension. It has been proposed that prostaglandins may be involved in the pathophysiology of bladder disorders. Therefore, antagonists of prostaglandin IP receptors are expected to be useful in the treatment of bladder disorders such as bladder outlet obstruction, urinary incontinence, reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity, urethritis, pelvic pain syndrome, prostatodynia, cystitis, idiophatic bladder hypersensitivity, and the like.

$PGI_2$ also acts on platelets and blood vessels to inhibit aggregation and to cause vasodilation, and is thought to be important for vascular homeostasis. It has been suggested that $PGI_2$ may contribute to the antithrombogenic properties of the intact vascular wall. $PGI_2$ is also thought to be a physiological modulator of vascular tone that functions to oppose the actions of vasoconstrictors, emphasized by the participation of $PGI_2$ in the hypotension associated with septic shock. Although prostaglandins do not appear to have direct effects on vascular permeability, $PGI_2$ markedly enhances edema formation and leukocyte infiltration by promoting blood flow in the inflamed region. Therefore, IP receptor antagonists may prevent conditions associated with excessive bleeding such as, but not limited to, hemophilia and hemorrhaging, may relieve hypotension related to septic shock, and may reduce edema formation.

Several in vivo analgesia studies in rodents suggest that $PGI_2$ plays a major role in the induction of hyperalgesia. Likewise, in vitro studies provide substantial evidence to suggest that "$PGI_2$-preferring" (IP) receptors act as important modulators of sensory neuron function (K. Bley et al, *Trends in Pharmacological Sciences* 1998, 19(4),141–147). Since IP receptors in sensory neurons are coupled to activation of both adenylyl cyclase and phospholipase C, and hence, cAMP-dependent protein kinase and protein kinase C, these receptors can exert powerful effects on ion channel activity and thus neurotransmitter release. Evidence of a prominent role for IP receptors in inflammatory pain has been obtained from recent studies in transgenic mice lacking the IP receptor (T. Murata et al., *Nature* 1997, 388, 678–682).

Antagonists of IP receptors are also expected to find a utility in respiratory allergies wherein $PGI_2$ production in response to an allergen is present, or in respiratory conditions such as asthma.

Additional information relating to prostaglandins and their receptors is described in Goodman & Gillman's, *The Pharmacological Basis of Therapeutics*, ninth edition, McGraw-Hill, New York, 1996, Chapter 26, pages 601–616. Thus antagonists which can selectively treat the above mentioned conditions by acting on the IP receptor, are desirable.

DESCRIPTION OF THE RELATED ART

U.S. application Ser. No. 09/810,436 assigned to Syntex LLC refers to certain carboxylic acid derivatives as IP antagonists.

U.S. Pat. No. 6,184,242 B1 assigned to Syntex LLC refers to certain imidazoline derivatives as IP antagonists.

U.S. Pat. No. 6,174,905 B1 and EP 974,576 assigned to Mitsui Chemicals, Inc. refer to certain benzoic acids used in a method of producing benzamide derivatives.

U.S. Pat. No. 5,998,424 assigned to DuPont Pharmaceuticals Co. refers to inhibitors of Factor Xa.

WO 00/06550 assigned to Nippon Soda Co. refers to new phenylazole compounds as lipid peroxidase inhibitors.

Bley et al., *Trends in Pharmacological Sciences* 1998, 19 (4), 141–147 refer to the role of IP prostanoid receptors in inflammatory pain.

Smith et al., *British Journal of Pharmacology* 1998, 124(3), 513–523 refer to characterization of prostanoid receptor-evoked responses in rat sensory neurons.

Murata. et al., *Nature* 1997, 388 (6643), 678–682 refer to altered pain perception and inflammatory response in mice lacking prostacyclin receptors.

Anderson et al., *Pharmacological Reviews* 1993, 45(3), 253–308 refer to Pharmacology of lower urinary tract smooth muscles and penile erectile tissues.

Coleman et al, *Pharmacological Review* 1994, 46(2), 205–229 refer to properties, distribution and structure of prostanoid receptors and their subtypes.

All publications, patents, and patent applications cited herein, whether supra or infra, are each hereby incorporated by reference in its entirety.

SUMMARY OF THE INVENTION

This invention relates to compounds comprising of the formula Formula I:

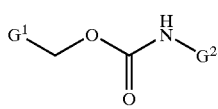

(I)

wherein:

$G^1$ is selected from the group consisting of a, $b^1$, and $b^2$;

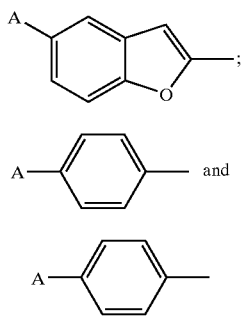

A is selected from the group consisting of phenyl, pyridinyl, pyrimidinyl, pyridinazinyl, pyrazinyl, and thienyl, all optionally substituted with lower alkyl, halogen, haloalkyl, alkoxy, cyano, nitro, —$SO_2R'$, —$NSO_2R'$, —$SO_2NR'R''$, —$NR'R''$, or —$COR'$;

R' and R" are each independently hydrogen or lower alkyl;

$G^2$ is selected from the group represented by the Formula c, d, e, and f;

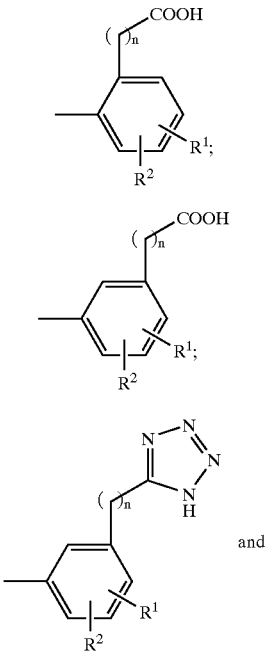

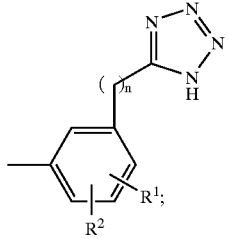

$R^1$ and $R^2$ are independently in each occurrence selected from the group consisting of hydrogen, lower alkyl, halogen, haloalkyl, nitro, —NR'R", —OR', —NR'$SO_2$R", —$SO_2$R', —COR', cyano, nitro, phenyl (optionally substituted with halo, alkyl, cyano, nitro, or alkoxy), or heteroaryl (optionally substituted with halo, alkyl, cyano, nitro, or alkoxy); and wherein R' and R" are as defined hereinbefore;

$R^1$ and $R^2$, if adjacent, taken together with the carbons to which they are attached may also form an aromatic ring, said ring being optionally substituted with one or two substitutents selected from the group consisting of lower alkyl, halo, cyano, or lower alkoxy;

n is an integer selected from 0, 1, 2 and 3;

or prodrugs, or pharmaceutically acceptable salts or solvates thereof.

In another aspect the invention relates to pharmaceutical compositions comprising a therapeutically effective amount of a compound of Formula I in admixture with at least one pharmaceutically acceptable carrier.

In another aspect, the invention relates to methods for treating a subject having a disease state that is alleviated by treatment with an IP receptor antagonist, which comprises administering to such a subject a therapeutically effective amount of at least one compound of Formula I. In a preferred embodiment, the disease state is associated with the urinary tract, pain, inflammation, respiratory states, edema formation, or hypotensive vascular diseases.

In another aspect, the invention relates to a process for preparing a compound of Formula I wherein $G^2$ is a group represented by the formulae c or d, which comprises:

esterification of the compounds having a general Formula 2 or 3:

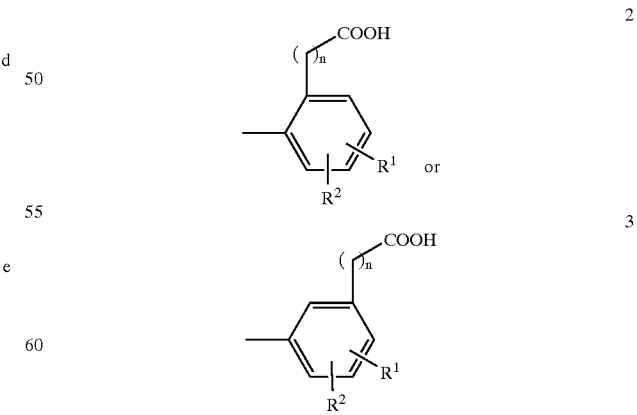

wherein n, $R^1$ and $R^2$ are as defined herein, acylation with phosgene, followed by reaction with a compound of general Formula 1

wherein G¹ is as defined herein, and hydrolysis, to provide a compound of the general Formula Ia or Ib

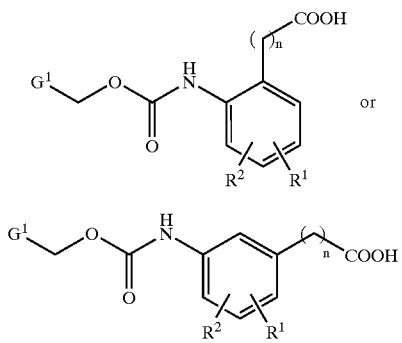

wherein n, G¹, R¹, and R² are as defined herein.

In another aspect, the invention relates to a process for preparing a compound of Formula I wherein G² is a group represented by the formulae c or d which comprises:

esterification of the compounds having a general Formula c or f which comprises:

acylation with phosgene of a compound of general Formula cm or co,

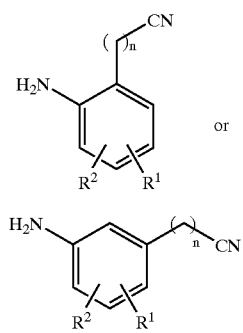

followed by reaction with a compound of general Formula 2

wherein G¹ is as defined herein, and treatment with azide to provide a compound of general Formula Ic

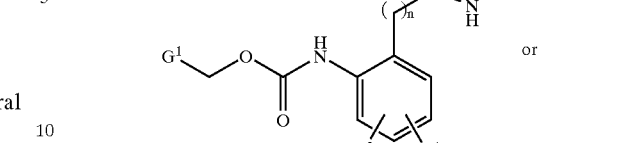

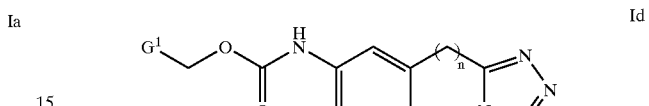

wherein n, G¹, R¹, and R² are as defined herein.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Lower alkyl" means the monovalent linear or branched saturated hydrocarbon radical, having from one to six carbon atoms inclusive, unless otherwise indicated. Examples of lower alkyl radicals include, but are not limited to, methyl, ethyl, propyl, isopropyl, 1-ethylpropyl, sec-butyl, tert-butyl, n-butyl, n-pentyl, n-hexyl, and the like.

"Alkoxy" means the radical —O—R, wherein R is a lower alkyl radical as defined herein. Examples of alkoxy radicals include, but are not limited to, methoxy, ethoxy, isopropoxy, and the like.

"Aryl" means the monovalent carbocyclic radical consisting of one individual ring, or one or more fused rings in which at least one ring is aromatic in nature, which can optionally be substituted with one or more, preferably one or two, substituents. Examples of aryl radicals include, but are not limited to phenyl, naphthyl, 4-fluorophenyl, and the like.

"Halogen", "halo" or "halide" means the radical fluoro, bromo, chloro, and/or iodo.

"Haloalkyl" means the lower alkyl radical as defined herein substituted in any position with one or more halogen atoms as defined herein. Examples of haloalkyl radicals include, but are not limited to, 1,2-difluoropropyl, 1,2-dichloropropyl, trifluoromethyl, 2,2,2-trifluoroethyl, 2,2,2-trichloroethyl, and the like.

"Heteroaryl" means the monovalent aromatic cyclic radical having one or more rings, preferably one to three rings, of four to eight atoms per ring incorporating one or more heteroatoms, preferably one or two, within the ring chosen from nitrogen, oxygen or sulfur), which can optionally be substituted with one or more, preferably one or two, substituents. Examples of heteroaryl radicals include, but are not limited to, imidazolyl, oxazolyl, thiazolyl, pyrazinyl, thienyl, furanyl, pyridinyl, pyrimidinyl, pyrazolyl, quinolinyl, isoquinolinyl, naphtyridinyl, and the like.

"Optionally substituted" or "opt. substituted" means that a group may or may not be substituted with one or more, preferably one or two substitutents independently selected from the specified group. For example phenyl optionally substituted with lower alkyl, alkoxy, halogen or cyano means that the phenyl group may or may not be substituted at any position with one or more, preferably one or two substituents independently selected from the group consisting of lower alkyl, alkoxy, halogen and cyano.

"Leaving group" means the group with the meaning conventionally associated with it in synthetic organic chemistry, i.e., an atom or group displaceable by a nucleophile. Examples of leaving groups include, but are not limited to, halogen, alkyl- or arylsulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral compound" means a compound with one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When chiral centers are present, the stereoisomers may be characterized by the absolute configuration (R or S) of the chiral centers. Absolute configuration refers to the arrangement in space of the substituents attached to a chiral center. The substituents attached to a chiral center under consideration are ranked in accordance with the *Sequence Rule* of Cahn, Ingold and Prelog. (Cahn et al. *Angew. Chem. Inter*. Edit 1966, 5, 385; errata 511; Cahn et al., *Angew. Chem.,* 1966, 78, 413; Cahn and Ingold *J. Chem. Soc.* (London), 1951, 612; Cahn et al., *Experientia,* 1956, 12, 81; Cahn, J., *Chem.Educ.,* 1964, 41, 116).

"Substantially pure" means at least about 80 mole percent, more preferably at least about 90 mole percent, and most preferably at least about 95 mole percent of the desired enantiomer or stereoisomer is present.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, 2,2,2-trifluoroacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

It should be understood that all references to pharmaceutically acceptable salts include solvent addition forms (solvates) or crystal forms (polymorphs) as defined herein, of the same acid addition salt.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate.

"Prodrug" means a pharmacologically inactive form of a compound which is metabolized in vivo, e.g., by biological fluids or enzymes, by a subject after administration into a pharmacologically active form of the compound in order to produce the desired pharmacological effect. The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Reference to a compound herein includes prodrug forms of a compound. Prodrugs are described in *The Organic Chemistry of Drug Design and Drug Action,* by Richard B. Silverman, Academic Press, San Diego, 1992, Chapter 8: "Prodrugs and Drug delivery Systems" pp.352–401; *Design of Prodrugs,* edited by H. Bundgaard, Elsevier Science, Amsterdam, 1985; *Design of Biopharmaceutical Properties through Prodrugs and Analogs,* Ed. by E. B. Roche, American Pharmaceutical Association, Washington, 1977; and *Drug Delivery Systems,* ed. by R. L. Juliano, Oxford Univ. Press, Oxford, 1980.

"Subject" means mammals and non-mammals. Mammals means any member of the Mammalia class including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, reptiles, and the like.

"Therapeutically effective amount" means an amount of a compound that, when administered to a subject for treating a disease state, is sufficient to effect such treatment for the disease state. The "therapeutically effective amount" will vary depending on the compound, and disease state being treated, the severity or the disease treated, the age and relative health of the subject, the route and form of administration, the judgement of the attending medical or veterinary practitioner, and other factors.

"Pharmacological effect" as used herein encompasses effects produced in the subject that achieve the intended purpose of a therapy. In one preferred embodiment, a pharmacological effect means that primary indications of the subject being treated are prevented, alleviated, or reduced. For example, a pharmacological effect would be one that results in the prevention, alleviation or reduction of primary indications in a treated subject. In another preferred embodiment, a pharmacological effect means that disorders or symptoms of the primary indications of the subject being treated are prevented, alleviated, or reduced. For example, a pharmacological effect would be one that results in the prevention or reduction of primary indications in a treated subject.

"Disease state" means any disease, condition, symptom, or indication.

"Treating" or "treatment" of a disease state includes:

(1) preventing the disease state, i.e. causing the clinical symptoms of the disease state not to develop in a subject that may be exposed to or predisposed to the disease state, but does not yet experience or display symptoms of the disease state.
(2) inhibiting the disease state, i.e., arresting the development of the disease state or its clinical symptoms, or
(3) relieving the disease state, i.e., causing temporary or permanent regression of the disease state or its clinical symptoms.

"Antagonist" means a molecule such as a compound, a drug, an enzyme inhibitor, or a hormone, that diminishes or prevents the action of another molecule or receptor site.

"Bladder disorders" include, but are not limited to, bladder outlet obstruction, urinary incontinence, reduced bladder capacity, frequency of micturition, urge incontinence, stress incontinence, reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity urethritis, pelvic pain syndrome, prostatodynia, cystitis or idiophatic bladder hypersensitivity.

"Bladder outlet obstruction" includes, but is not limited to, benign prostatic hypertrophy (BPH), urethral stricture disease, tumors and the like. It is usually symptomatically manifested as obstructive (low flow rates, difficulty in initiating urination, and the like), or irritative (urgency, suprapubic pain, and the like).

"Outlet insufficiency" includes, but is not limited to, urethral hypermobility, intrinsic sphincteric deficiency, or mixed incontinence. It is usually symptomatically manifested as stress incontinence.

"Pelvic Hypersensitivity" includes but is not limited to, pelvic pain, interstitial (cell) cystitis, prostadynia, prostatis, vulvadynia, urethritis, orchidalgia, and the like. It is symptomatically manifested as pain, inflammation or discomfort referred to the pelvic region, and usually includes symptoms of overactive bladder.

"Pain" means the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (*Dorland's Illustrated Medical Dictionary*, 28<sup>th</sup> Edition, W. B. Saunders Company, Philadelphia, Pa.). The goal of treatment of pain is to reduce the degree of severity of pain perceived by a treatment subject.

Throughout the application the following abbreviations are used with the following meanings:

| BINAP | 2,2'-Bis(diphenylphosphino)1,1'-binaphthyl |
|-------|--------------------------------------------|
| DIBAL | Diisobutylaluminum chloride |
| DCC | 1,3-Dicyclohexylcarbodiimide |
| DMAP | 4-Dimethylaminopyridine |
| DMF | N,N-Dimethylformamide |
| DMSO | Dimethylsulfoxide |
| EtOAc | Ethyl Acetate |
| EtOH | Ethanol |
| THF | Tetrahydrofuran |

Nomenclature

In general, the nomenclature used in this Application is based on AUTONOM™ v.4.0, a Beilstein Institute computerized system for the generation of IUPAC systematic nomenclature.

For example, a compound of Formula I wherein $G^1$ is a group of Formula a, A is phenyl, $G^2$ is a group of Formula c, wherein n is 0 and $R^1$ and $R^2$ are hydrogen, is named 2-(5-phenyl-benzofuran-2-ylmethoxycarbonylamino)-benzoic acid.

A compound of Formula I wherein $G^1$ is a group of Formula a, A is phenyl, $G^2$ is a group of Formula e, wherein n is 0, $R^1$ is p-phenyl, and $R^2$ is hydrogen, is named [3-(1H-tetrazol-5-yl)-biphenyl-4-yl]-carbamic acid 5-phenyl-benzofuran-2-ylmethyl ester.

Preferred Compounds

Among compounds of the present invention set forth in the Summary of the Invention, certain compounds of Formula I, or individual isomers, racemic or non-racemic mixtures of isomers, or pharmaceutically acceptable salts or solvates thereof, are preferred.

For example, preferred compounds of Formula I include those wherein $G^1$ is selected from the group consisting of a, $b^1$, and $b^2$, preferably from the group a.

Preferred compounds of Formula I include those wherein A is preferably selected from the group consisting of phenyl, pyridinyl, pyrimidinyl, and thienyl, preferably phenyl pyrimidinyl, and pyridinyl, all optionally substituted as described in the Summary of the Invention.

Preferred compounds of Formula I also include those wherein, $G^2$ is selected from the group consisting of c, d, e, and f, preferably from the group c, d, and e, more preferably from the group c and e.

Preferred compounds of Formula I also include those wherein $R^1$ and $R^2$ are each independently in each occurrence selected from the group consisting of hydrogen, lower alkyl, haloalkyl, halogen, cyano, nitro, —OR', —SO₂R', —NR'SO₂R", —COR', —NR'R", optionally substituted phenyl, and optionally substituted heteroaryl; and $R^1$ and $R^2$, if adjacent, taken together with the carbons to which they are attached may form an aromatic ring, optionally substituted with one or two substitutents selected from the group consisting of lower alkyl, halogen, cyano, and lower alkoxy. More preferably $R^1$ and $R^2$ are each independently in each occurrence hydrogen, lower alkyl, halogen, cyano, nitro, —OR', —SO₂R', —NR'SO₂R", —COR', or —NR'R". Other preferred compounds of Formula I also include those wherein $R^1$ and $R^2$ are each independently in each occurrence selected from the group consisting of optionally substituted phenyl, optionally substituted thienyl and optionally substituted pyridinyl, and $R^1$ and $R^2$, if adjacent, taken together with the carbons to which they are attached may form an aromatic ring, optionally substituted with one or two substitutents selected from the group consisting of lower alkyl, halogen, cyano, and lower alkoxy. Other preferred compounds of Formula I also include those wherein $R^1$ and $R^2$ are each independently in each occurrence selected from the group consisting of hydrogen, lower alkyl, halogen, cyano, nitro, —OR', —SO$_2$R', —NR'SO$_2$R", —COR', and —NR'R".

In one embodiment compounds of Formula I, are those wherein $G^2$ is selected from the group represented by the Formula c and d. Another set of compounds of Formula I, is that wherein $G^1$ is selected from the group represented by the Formula a, and $G^2$ is selected from the group represented by the Formula c and d, and within this embodiment another set of compounds is that wherein A is phenyl optionally substituted with lower alkyl, halogen, haloalkyl, alkoxy, cyano, nitro, —SO$_2$R', —NR'SO$_2$R", —SO$_2$NR'R",—COR', and —NR'R", and R' and R" are each independently hydrogen or lower alkyl. In another embodiment $G^2$ is a group represented by the Formula c, and within this embodiment a set of compounds is that wherein $R^1$ is selected from the group consisting of hydrogen, lower alkyl, halogen, cyano, nitro, —OR', —SO$_2$R', —NR'SO$_2$R", —COR', and —NR'R", and R' and R" are each independently hydrogen or lower alkyl; another set of compounds is that wherein $R^1$ is phenyl, which is optionally substituted with halogen, lower alkyl, cyano, nitro or alkoxy; another set of compounds is that wherein $R^1$ is pyridinyl which is optionally substituted with halogen, lower alkyl, cyano, nitro or alkoxy; another set of compounds is that wherein $R^1$ is thienyl, which is optionally substituted with halogen, lower alkyl, cyano, nitro or alkoxy; and in another set of compounds is that wherein $R^1$ and $R^2$, if adjacent, taken together with the carbons to which they are attached form an aromatic ring, which is optionally substituted with halogen, lower alkyl, cyano, nitro or alkoxy.

In another embodiment the compounds of Formula I, are those wherein $G^1$ is a group represented by Formula a, $G^2$ is a group represented by the Formula c and A is pyridinyl, and within this embodiment one set of compounds is that wherein $R^1$ is selected from the group consisting of hydrogen, lower alkyl, halogen, cyano, nitro, —OR', —SO$_2$R', —NR'SO$_2$R", —COR', and —NR'R", and R' and R" are each independently hydrogen or lower alkyl; and another set is that wherein $R^1$ is phenyl optionally substituted with lower alkyl, halogen, haloalkyl, alkoxy, cyano, nitro, —SO$_2$R', —NR'SO$_2$R", —SO$_2$NR'R", —NR'R", or —COR', and R' and R" are each independently hydrogen or lower alkyl.

In another embodiment the compounds of Formula I compounds are those wherein $G^1$ is a group represented by Formula a, $G^2$ is a group represented by the Formula c, and A is pyridiminyl, which is optionally substituted with halogen, alkyl, cyano, nitro, or alkoxy; and within this embodiment a set of compounds is that wherein $R^1$ is selected from the group consisting of hydrogen, lower alkyl, halogen, cyano, nitro, —OR', —SO$_2$R', —NR'SO$_2$R", —COR', and —NR'R", and R' and R" are each independently hydrogen or lower alkyl.

In another embodiment the compounds of Formula I is a set of compounds wherein $G^2$ is selected from the group represented by the Formula e and f.

In another embodiment the preferred compounds of Formula I are those wherein $G^1$ is a group of formula a, and $G^2$ is a group represented by the Formula e; and within this embodiment one set of compounds is that wherein A is phenyl optionally substituted with lower alkyl, halogen, haloalkyl, alkoxy, cyano, nitro, —SO$_2$R', —NR'SO$_2$R", —SO$_2$NR'R", —NR'R", or —COR', $R^1$ is selected from the group consisting of hydrogen, lower alkyl, halogen, cyano, nitro, —OR', —SO$_2$R', —NR'SO$_2$R", —COR', and —NR'R", and R' and R" are each independently hydrogen or lower alkyl; and another set of compounds is that wherein A is phenyl optionally substituted lower alkyl, halogen, haloalkyl, alkoxy, cyano, nitro, —SO$_2$R', —NR'SO$_2$R", —SO$_2$NR'R", —NR'R", or —COR'; R' and R" are each independently hydrogen or lower alkyl; and $R^1$ is phenyl optionally substituted with halogen, alkyl, cyano, nitro, or alkoxy.

In another embodiment the compounds of Formula I are those wherein $G^1$ is a group represented by the Formula $b^1$, and within this embodiment a set of compounds is that wherein $G^2$ is a group represented by the Formula c. Another set of compounds of Formula I are those wherein $G^1$ is a group represented by the Formula $b^1$, $G^2$ is a group represented by the Formula c, and A is phenyl optionally substituted with lower alkyl, halogen, haloalkyl, alkoxy, cyano, nitro, —SO$_2$R', —NR'SO$_2$R", —SO$_2$NR'R", —NR'R", or —COR'; and R' and R" are each independently hydrogen or lower alkyl, and within this embodiment a set of compounds is that wherein A is phenyl optionally substituted with lower alkyl, halogen, haloalkyl, alkoxy, cyano, nitro, —SO$_2$R', —NR'SO$_2$R", —SO$_2$NR'R", —NR'R", or —COR'; and R' and R" are each independently hydrogen or lower alkyl.

In another embodiment a set of compounds of Formula I is that wherein $G^1$ is selected from the group represented by Formula $b^2$; and within this embodiment another set of compounds is that wherein $G^2$ is selected from the group represented by the Formula c. Another set of compounds of Formula I is that wherein $G^1$ is selected from the group represented by Formula $b^2$, $G^2$ is selected from the group represented by the Formula c, and A is phenyl optionally substituted with lower alkyl, halogen, haloalkyl, alkoxy, cyano, nitro, —SO$_2$R', —NR'SO$_2$R", —SO$_2$NR'R", —NR'R", or —COR'; and R' and R" are each independently hydrogen or lower alkyl; and within this embodiment a different set of compound is that wherein $R^1$ is selected from the group consisting of hydrogen, lower alkyl, halogen, cyano, nitro, —OR', —SO$_2$R', —NR'SO$_2$R", —COR', and —NR'R", and R' and R" are each independently hydrogen or lower alkyl.

Exemplary particularly preferred compounds, or individual isomers, racemic or non-racemic mixtures of isomers, or pharmaceutically acceptable salts or solvates thereof, include:

4-(5-phenyl-benzofuran-2-ylmethoxycarbonylamino)-biphenyl-3-carboxylic acid;

4'-fluoro-4-(5-phenyl-benzofuran-2-ylmethoxycarbonylamino)-biphenyl-3-carboxylic acid;

4'-fluoro-4-[5-(4-fluoro-phenyl)-benzofuran-2-ylmethoxycarbonylamino]-biphenyl-3-carboxylic acid;

2-(5-phenyl-benzofuran-2-ylmethoxycarbonylamino)-naphthalene-1-carboxylic acid;

2-[5-(4-fluoro-phenyl)-benzofuran-2-ylmethoxycarbonylamino]-5-isopropoxy-benzoic acid;

2-[5-(4-fluoro-phenyl)-benzofuran-2-ylmethoxycarbonylamino]-6-methyl-benzoic acid;

2-[5-(4-fluoro-phenyl)-benzofuran-2-ylmethoxycarbonylamino]-5-pyridin-3-yl-benzoic acid;

5-methanesulfonyl-2-(5-phenyl-benzofuran-2-ylmethoxycarbonylamino)-benzoic acid;

4-[5-(4-fluoro-phenyl)-benzofuran-2-ylmethoxycarbonylamino]-biphenyl-3-carboxylic acid;

2-(5-phenyl-benzofuran-2-ylmethoxycarbonylamino)-5-thiophen-3-yl-benzoic acid;

5-bromo-2-(5-phenyl-benzofuran-2-ylmethoxycarbonylamino)-benzoic acid;

[3-(1H-tetrazol-5-yl)-biphenyl-4-yl]-carbamic acid 5-phenyl-benzofuran-2-ylmethyl ester;

[2-(1H-tetrazol-5-yl)-phenyl]-carbamic acid 5-phenyl-benzofuran-2-ylmethyl ester;

2-chloro-6-[5-(4-fluoro-phenyl)-benzofuran-2-ylmethoxycarbonylamino]-benzoic acid;

2-[5-(4-fluoro-phenyl)-benzofuran-2-ylmethoxycarbonylamino]-naphthalene-1-carboxylic acid;

2-[5-(4-fluoro-phenyl)-benzofuran-2-ylmethoxycarbonylamino]-5-methanesulfonylamino-benzoic acid;

[2-(5-phenyl-benzofuran-2-ylmethoxycarbonylamino)-phenyl]-acetic acid;

2-[2-(biphenyl-4-yloxy)-ethoxycarbonylamino]-6-chloro-benzoic acid; or 2-chloro-6-(5-pyrimidin-5-yl-benzofuran-2-ylmethoxycarbonylamino)-benzoic acid.

General Synthetic Reaction Schemes

Compounds of the present invention may be made by the methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis;* Wiley & Sons: New York, 1991, Volumes 1–15; *Rodd's Chemistry of Carbon Compounds,* Elsevier Science Publishers, 1989, Volumes 1–5 and Supplementals; and *Organic Reactions,* Wiley & Sons: New York, 1991, Volumes 1–40. The following synthetic reaction schemes are merely illustrative of some methods by which the compounds of the present invention may be synthesized, and various modifications to these synthetic reaction schemes may be made and will be suggested to one skilled in the art having referred to the disclosure contained in this Application.

The starting materials and the intermediates of the synthetic reaction schemes may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein preferably take place at atmospheric pressure over a temperature range from about −78° C. to about 150° C., more preferably from about 0° C. to about 125° C., and most preferably and conveniently at about room (or ambient) temperature, e.g., about 20° C.

In general, the compounds of Formula I are prepared following the method described in Schemes A, B, and C.

Scheme A

Scheme A describes a method of preparing a compound of Formula I as described in the Summary of the Invention, wherein $G^2$ is a group represented by Formula c; and n, $G^1$, $R^1$, $R^2$, and c are as defined in the Summary of the Invention.

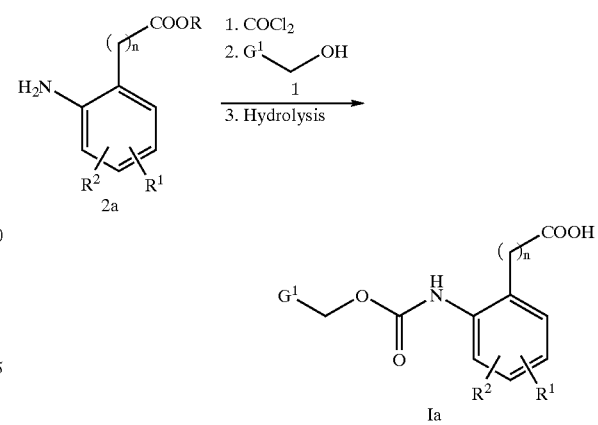

Generally as set forth in Scheme A, a 2-aminobenzoate of general Formula 2a can be acylated with phosgene in an inert solvent to give the isocyanate that can subsequently react with a hydroxymethyl derivative of general Formula 1, to give the carbamate-carboxyl ester derivative that after hydrolysis of the carboxyl ester group can yield a benzoic acid of Formula Ia. The acylation with phosgene is well described in the art, for example in Ozaki, *Chem.Rev.* 1972, 72, 457–496. The condensation of the isocyanate with the hydroxymethyl derivative can be effected in the presence of a base for example triethylamine or 4-dimethylaminopyridine (DMAP). Hydrolysis of the ester can be effected with an alkali hydroxyde such as sodium, lithium or potassium hydroxyde in a lower alkanol solution to prepare the acid of Formula Ia.

Scheme for the preparation of compounds of Formula 1

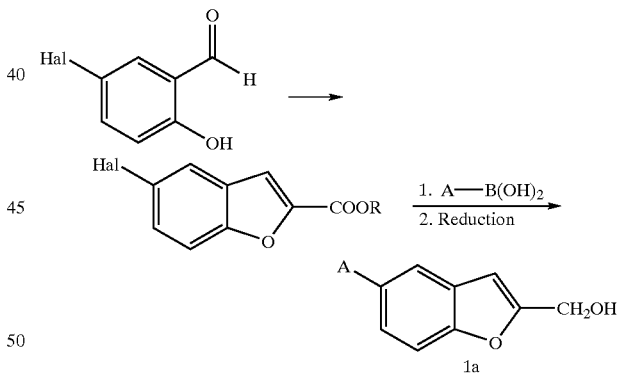

Generally compounds of Formula 1a, which are compounds of Formula 1, wherein $G^1$ is group represented by Formula a, can be prepared from 5-halo-benzofuran-2-carboxylate, wherein R is a lower alkyl, such as methyl, and Hal is a halide such as a bromo or iodo group. with the appropriate boronic acid in the presence of a catalyst preferably tetrakis-triphenylphosphine-palladium and a base such as sodium carbonate or potassium carbonate, followed by reduction of the acid with for example, lithium aluminum hydride or borohydride in a suitable solvent such as THF, diethyl ether or 1,2-dimethoxyethane. The synthesis of 5-bromobenzofuran-2-carboxylate can be effected from 5-bromosalicylaldehyde and diethylbromomalonate in the presence of a base such as potassium carbonate.

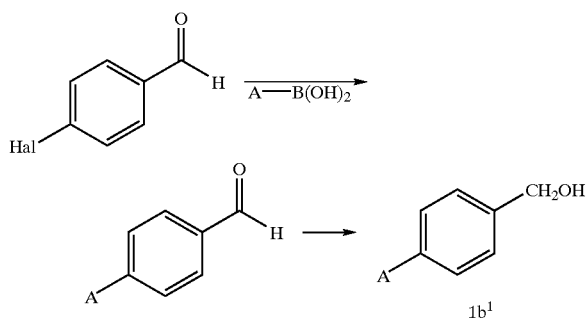

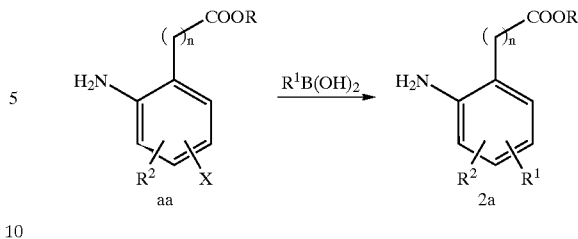

Alternatively compounds of Formula 1b$^1$, which are compounds of Formula 1, wherein G$^1$ is a group represented by Formula b$^1$, are commercially available or can be prepared by reacting 4-halo-benzaldehyde with the appropriate borane derivative followed by hydrogenation or reduction, with for example sodium borohydride, of the aldehyde group to yield the appropriate phenyl methanol derivative. Such procedures are well described in the art, for example in Zhang et al., *Tetrahedron Lett.*, 1999, 40, 32, 5813–5816.

For example, amines of Formula 2a wherein R$^1$ is phenyl or heteroaryl, can be prepared from the halobenzoate starting material of general Formula aa wherein X is a halide group, with a boronic acid of general Formula R$^1$B(OH)$_2$, in the presence of a catalyst preferably tetrakis-triphenylphosphine-palladium and a base such as sodium carbonate, potassium carbonate, or potassium phosphate in a solvent such as for example toluene, 1,2-dimethoxyethane, THF, or dioxane. Such procedures have been described for example in *Synth. Commun.*, 1981, 11, 513 and in *Chem. Rev.*, 1995, 95, 257.

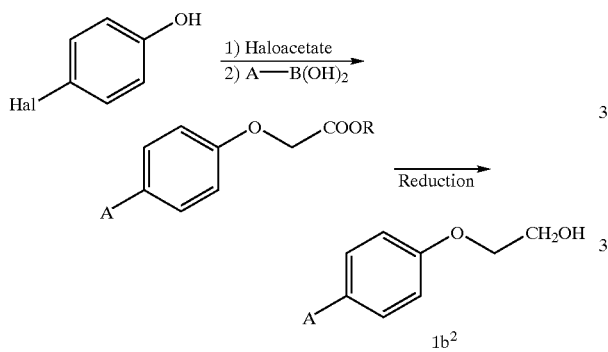

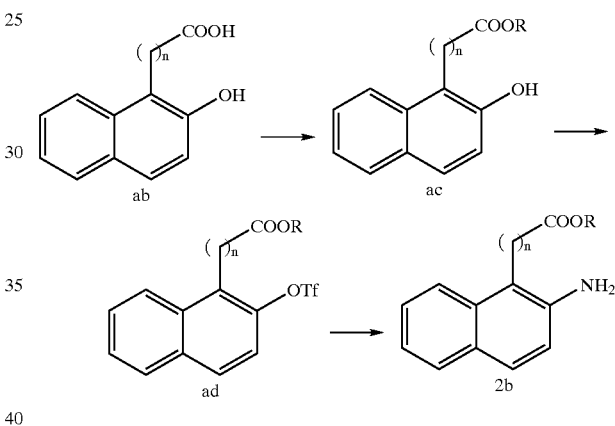

Alternatively compounds of Formula 1b$^2$, which are compounds of Formula 1, wherein G$^1$ is a group represented by Formula b$^2$, can be prepared by reacting a 4-halophenol, preferably 4-bromophenol or 4-iodophenol, with a haloacetate of general Formula Hal-C(O)OR wherein Hal is halogen and R is lower alkyl, preferably methyl bromoacetate, in the presence of a base, to afford a 4-halophenoxy acetate which following condensation with the appropriate borane derivative of general Formula A-B(OH)$_2$ can afford the 4-substituted phenyloxy acetate derivative intermediate. Reduction with for example, lithium aluminum hydride or borohydride in a suitable solvent such as THF, diethyl ether or 1,2-dimethoxyethane can afford the desired alcohol of general Formula 1b$^2$. Alternatively if the compound of general Formula 1b$^2$ wherein A is phenyl is desired, 4-phenylphenol can be used as starting material to be alkylated with a haloacetate as described above, to prepare the intermediate biphenyl-4-yloxy-acetic acetate that following reduction can afford the desired alcohol of Formula 1b2 wherein A is phenyl.

Scheme for the Preparation of Compounds of Formula 2

Certain amines of general Formula 2, which are amines of general Formula G$^2$NH$_2$, wherein G$^2$ is a group represented by Formula c, are available commercially, others can be prepared using methods familiar to the skilled artisan.

Alternatively compounds of Formula 2b, wherein R$^1$ and R$^2$, form a six membered aromatic ring can be prepared from the 2-hydroxynaphthoic acid of Formula ab. Esterification in the presence of a base such as triethylamine or 4-dimethylaminopyridine in the presence of a dehydrating agent such as DCC, with for example 2-trimethylsilylethanol can yield the protected hydroxy acid of general Formula ac. The hydroxy group is converted into a reactive ester, preferably a trifluoromethanesulfonate of general Formula ad, which undergoes a palladium catalyzed aromatic amination in the presence of benzophenone imine to yield after acid hydrolysis the aminocarboxylic ester of Formula 2b, wherein R is for example trimethylsilylethyl. Appropriate solvents can be for example THF, dioxane or 1,2-dimethoxyethane.

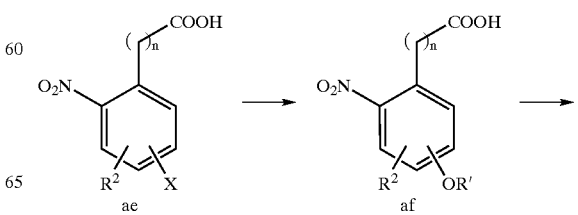

-continued

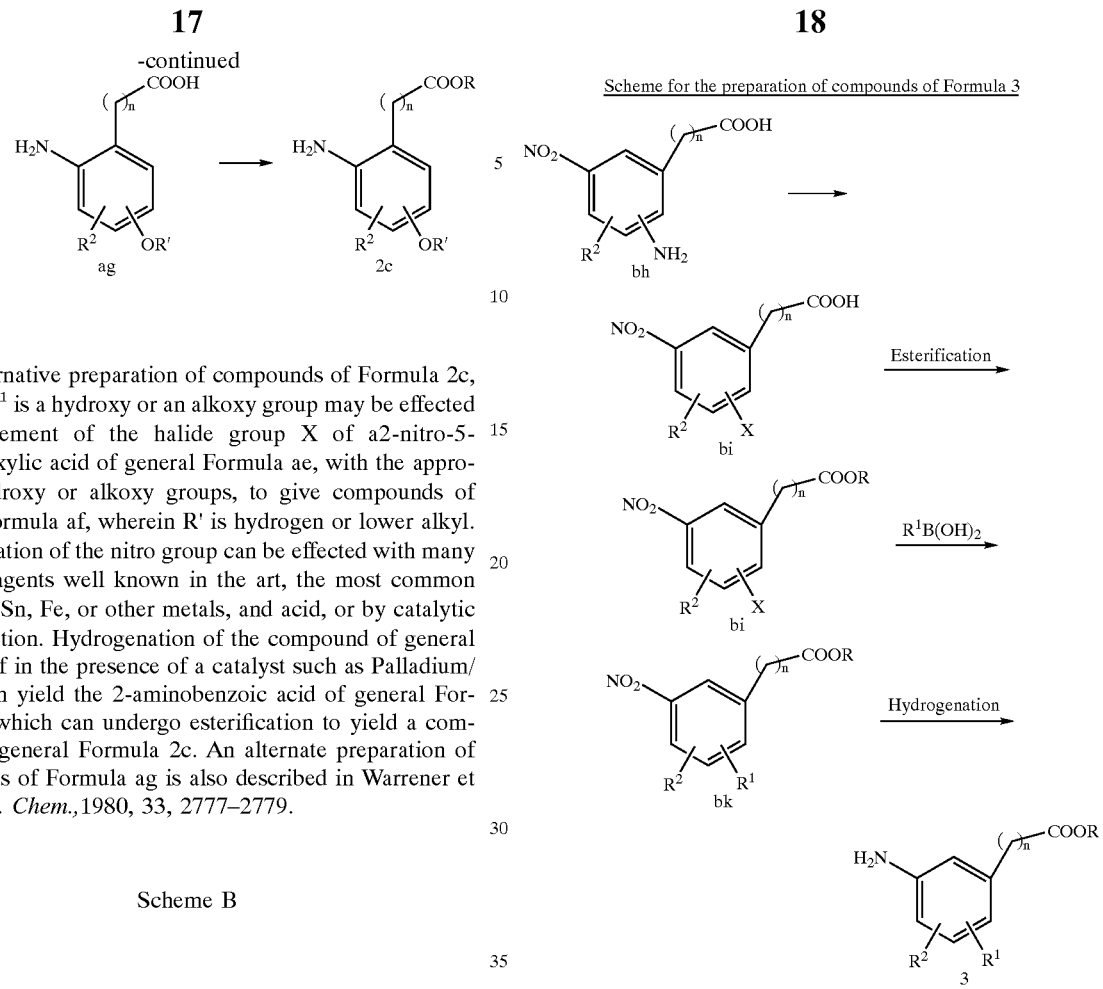

Scheme for the preparation of compounds of Formula 3

An alternative preparation of compounds of Formula 2c, wherein $R^1$ is a hydroxy or an alkoxy group may be effected by replacement of the halide group X of a2-nitro-5-halocarboxylic acid of general Formula ae, with the appropriate hydroxy or alkoxy groups, to give compounds of general Formula af, wherein R' is hydrogen or lower alkyl. Hydrogenation of the nitro group can be effected with many reducing agents well known in the art, the most common being Zn, Sn, Fe, or other metals, and acid, or by catalytic hydrogenation. Hydrogenation of the compound of general Formula af in the presence of a catalyst such as Palladium/carbon can yield the 2-aminobenzoic acid of general Formula ag, which can undergo esterification to yield a compound of general Formula 2c. An alternate preparation of compounds of Formula ag is also described in Warrener et al, *Aust. J. Chem.*, 1980, 33, 2777–2779.

Scheme B

Scheme B describes a method of preparing a compound of Formula I wherein $G^2$ is a compound represented by Formula d, wherein n, $G^1$, $R^1$, $R^2$ and d are as defined in the Summary of the Invention.

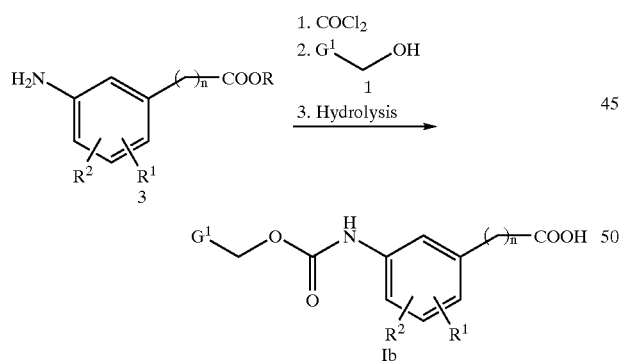

Generally as set forth in Scheme B, following the procedure described supra, a 3-aminobenzoate of general Formula 3 can be acylated with phosgene in an inert solvent to give the isocyanate that can subsequently react with a hydroxymethanol of general Formula 1, to give the carbamate-carboxyl ester derivative that after hydrolysis of the carboxyl ester group can yield a benzoic acid of Formula Ib.

Preparation of compounds of general Formula 3, can be effected by reduction of the 3-nitrobenzoic acid derivative of general Formula bk, following the procedure described in Scheme A for compounds of general Formula ag. Compounds of general Formula bk, wherein $R^1$ is phenyl or heteroaryl can be prepared from the commercially available 3-nitrobenzoic acid derivatives of general Formula bh, followed by replacement of the amino group by an halide to yield a compound of Formula bi, which after esterification of the acid group and reaction with a boronic acid of general Formula $R^1B(OH)_2$, in the presence of a catalyst preferably tetrakis-triphenylphosphine-palladium and a base such as sodium carbonate or potassium carbonate, can yield a compound of general Formula bk.

Scheme C

Scheme C describes a method of preparing a compound of Formula I wherein $G^2$ is a compound represented by Formula e or f, wherein e or f, n, $G^1$, $R^1$, and $R^2$, are as defined in the Summary of the Invention.

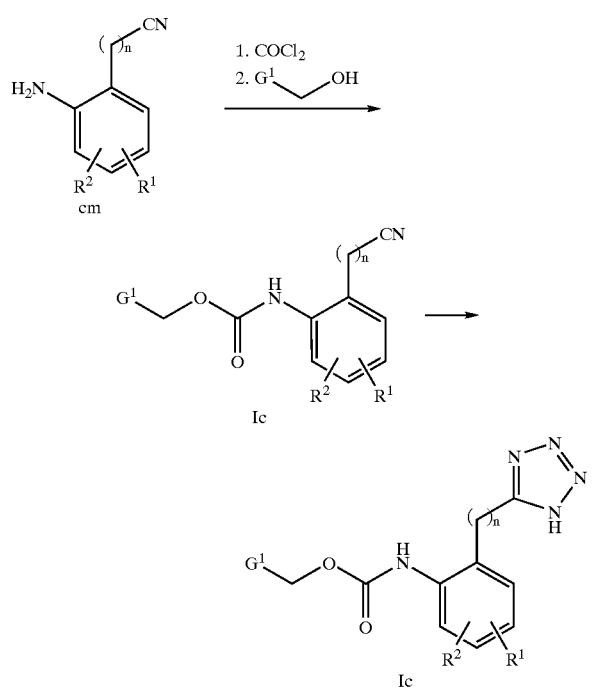

Generally as set forth in Scheme C, a certain aminobenzonitrile of general Formula cm can be acylated with phosgene in an inert solvent to give the isocyanate that can subsequently react with a hydroxymethanol of general Formula 1, to give the carbamate of general Formula cn, under similar conditions as described in Schemes A and B. Treatment of the nitrile group with sodium azide can yield the tetrazolyl derivative of general Formula Ic. Compounds of general Formula cm, wherein $R^1$ is phenyl or heteroaryl can be prepared from the appropriate starting halo-amino-nitrile derivative with phenyl or heteroaryl boronic acid in the presence of a catalyst preferably tetrakis-triphenylphosphine-palladium and a base such as sodium carbonate or potassium carbonate.

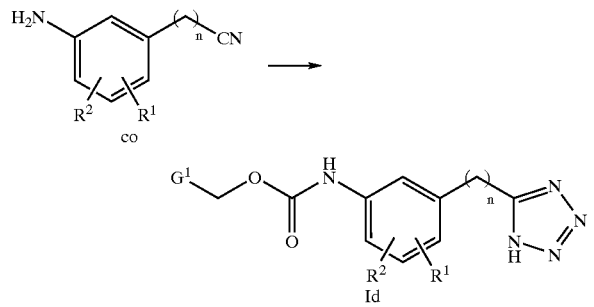

Similarly as set forth herein a compound of Formula Id can be prepared from a compound of Formula co.

General Utility

The IP receptor antagonists such as those described in this invention preferably possess utility in bladder disorders associated with bladder outlet obstruction and urinary incontinence conditions such as bladder outlet obstruction, urinary incontinence, reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity, urethritis, pelvic pain syndrome, prostatodynia, cystitis, and idiopathic bladder hypersensitivity.

Preferred compounds also possess anti-inflammatory and/or analgesic properties in vivo. Accordingly, preferred compounds are useful as anti-inflammatory and/or analgesic agents in mammals, especially humans. They find utility in pain conditions from a wide variety of causes, including but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

Preferred compounds also find utility in inflammatory conditions from a variety of causes, including but not limited to, bacterial, fungal or viral infections, rheumatoid arthritis, osteoarthritis, surgery, bladder infection or idiopathic bladder inflammation, over-use, old age, or nutritional deficiencies, prostatitis, and conjunctivitis.

Preferred compounds also find utility in the treatment of hypotensive vascular diseases such as hypotension associated with septic shock.

In addition, preferred compounds also find utility in the treatment of respiratory diseases such as allergies and asthma.

These and other therapeutic uses are described, for example, in *Goodman & Gilman's, The Pharmacological Basis of Therapeutics*, ninth edition, McGraw-Hill, New York, 1996, Chapter 26:601–616; and Coleman, R. A., *Pharmacological Reviews*, 1994, 46, 205–229.

Testing

The binding affinity of these compounds to the intended target may be measured with the in vitro Human Platelet IP receptor binding Assay as described in more detail in Example 16. The inhibition of bladder contractions of this invention may be assayed by in vivo assays such as Inhibition of Bladder Contractions Induced by Isovolumetric Bladder Distension in Rats and Inhibition of Volume-Induced Contractions in Rats, as described in more detail in Examples 19 and 20 respectively. The anti-inflammatory/analgesic activity of the compounds of this invention may be assayed by in vivo assays such as the Rat Carrageenan Paw Assay, the Rat Complete Freund's Adjuvant-induced Assay, and the Carbaprostacyclin Induced Writhing Test as described in more detail in Examples 17, 18, and 22 respectively. Activity in the inhibition of the septic shock may be assayed by in vivo assays such as the Rat Reversal of Endotoxin-Induced Hypotension Assay, as described in more detail in Example 21.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa. Representative pharmaceutical formulations containing a compound of the present invention are described in Examples 9–15.

EXAMPLES

The following preparations and examples are given to enable those skilled in the art to more clearly understand and to practice the present invention. They should not be considered as limiting the scope of the invention, but merely as being illustrative and representative thereof.

Preparation 1

(5-Phenyl-benzofuran-2-yl)-methanol

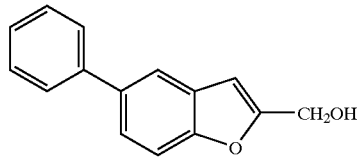

Preparation of a Compound of Formula 1 wherein $G^1$ is (a) and A is Phenyl.

Step 1:
Ethyl 5-bromo-benzofuran-2-carboxylate

A mixture of 5-bromosalicylaldehyde (10 g, 50 mmol), diethyl bromomalonate (13.1 g, 55 mmol), potassium carbonate (6.9 g, 50 mmol), and 2-butanone (80 mL) was stirred at 90° C. for 16 h. The solvent was removed under reduced pressure at 45° C., and the residue was acidified with 1M HCl, extracted, washed, dried, and evaporated. The residue was purified by chromatography to give 3.6 g of ethyl 5-bromo-benzofuran-2-carboxylate, mp. 59–60° C.

Step 2:
5-Phenyl-benzofuran-2-carboxylic acid

A mixture of ethyl 5-bromo-benzofuran-2-carboxylate (2.5 g, 9.3 mmol), benzeneboronic acid (1.25 g, 10.2 mmol), tetrakis(triphenylphosphine)palladium (0) (118 mg), sodium carbonate (3.25 g, 30.6 mmol) in water (25 mL), and dioxane (25 mL) was stirred under an argon atmosphere and heated to 100° C. for 16 h. The white heterogeneous mass was acidified with 1M HCl, extracted, washed, dried, and evaporated, to give 2.2 g of 5-phenyl-benzofuran-2-carboxylic acid, mp. 218–220° C.

Step 3:
(5-Phenyl-benzofuran-2-yl)-methanol

A solution of 5-phenyl-benzofuran-2-carboxylic acid (2.1 g, 8.8 mmol) dissolved in THF (50 mL) was cooled to 5° C. in an ice bath, and LiAlH$_4$ (0.67 g, 17.6 mmol) was added portionwise and stirred at room temperature for 1.5 hrs. The excess reagent was decomposed with an addition of 1M HCl, and the acidified mixture was extracted with ethyl acetate, washed, dried, and evaporated. The residue was purified by chromatography to give about 1.22 g of (5-phenyl-benzofuran-2-yl)-methanol, mp. 134–135° C.

Similarly following this procedure, but replacing benzene boronic acid with the appropriate heteroaryl borane derivatives the following compounds of general Formula 1 were prepared:
(5-pyridinyl-3-ylbenzofuran-2-yl) methanol;
(5-thiophen-3-yl-benzofuran-2-yl) methanol; and
(5-pyrimidinyl-2-ylbenzofuran-2-yl) methanol.

Preparation 2

(5-Pyridin-2-yl-benzofuran-2-yl)-methanol

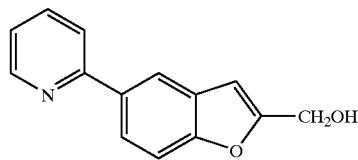

Preparation of a Compound of Formula 1 wherein $G^1$ is (a) and A is pyridin-2-yl. 5-Pyridin-2yl-benzofuran-2-carboxylic acid A mixture of ethyl 5-bromo-benzofuran-2-carboxylate (1.0 g, 3.8 mmol), (prepared as described herein in Preparation1), 2-pyridinyl zinc bromide (15 mL, 7.5 mmol), tetrakis(triphenylphosphine)palladium (0) (100 mg), was stirred under an argon atmosphere and heated to 60° C. overnight. The mixture was cooled, poured into water, extracted with ethyl acetate, washed with brine, dried ($MgSO_4$), and evaporated. Purification by chromatography gave 770 mg of 5-pyridin-2yl-benzofuran-2-carboxylic acid.
(5-Pyridin-2-yl-benzofuran-2-yl)-methanol To a solution of 5-pyridin-2yl-benzofuran-2-carboxylic acid (770 mg, 2.9 mmol) in 28 mL t-butanol and 2.5 mL methanol was added $NaBH_4$ (275 mg, 7.2 mmol). The mixture was heated at 50° C. under argon overnight, allowed to cool, poured into brine, extracted with ethyl acetate, washed with brine, dried ($MgSO_4$), and evaporated. Purification by chromatography gave 404 mg of (5-pyridin-2-yl-benzofuran-2-yl)-methanol. MS: $(M+H)^+$=226.

Preparation 3

(5-Pyrazin-2-yl-benzofuran-2-yl)-methanol

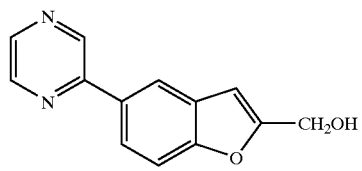

Preparation of a Compound of Formula 1 wherein $G^1$ is (a) and A is pyrazin-2-yl.
Step 1:
(5-Bromo-benzofuran-2-yl)-methanol To a solution of ethyl 5-bromo-benzofuran-2-carboxylate (5 g; 18.6 mmol) in 65 mL THF under nitrogen, was added DIBAL (46 mL, 46 mmol) dropwise over 30 minutes, then stirred overnight at room temperature. After dropwise addition of 25 mL of water, the mixture was evaporated, extracted with ethyl acetate, filtered, washed, dried ($MgSO_4$) and evaporated to yield 4.2 g of crude product which was further purified by chromatography to afford (5-bromo-benzofuran-2-yl)-methanol.
Step 2
(5-Pyrazin-2-yl-benzofuran-2-yl)-methanol To a solution of (5-bromo-benzofuran-2-yl)-methanol (1 g, 4.4 mmol) and 2-tributylstannylpyrazine (1.6 g, 3.7 mmol) in 15 mL toluene at room temperature under argon, was added tetrakis(triphenylphosphine)palladium (0) (130 mg), and the mixture was heated at 95° C. overnight. The precipitate was allowed to cooled, extracted with ethyl acetate, washed with brine and dried over $MgSO_4$. Filtration afforded 2.1 g of crude product that was further purified by chromatography to afford (5-pyrazin-2-yl-benzofuran-2-yl)-methanol.

Preparation 4

(5-Pyridazin-4-yl-benzofuran-2-yl)-methanol

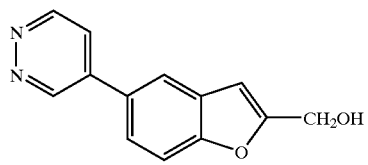

Preparation of a Compound of Formula 1 wherein $G^1$ is (a) and A is pyridazin-4-yl.

To a 6% solution of 14 g (10 mmol) of tetrazine, prepared as described in *J. Heterocycl. Chem* 1987, 24 (3), 545–8, in methylene chloride under nitrogen was added dropwise tributyl(ethynyl)tin (3.6 mL; 12 mmol), and the mixture was stirred overnight at room temperature. Evaporation afforded 4-tert-butylstannanyl-pyridazine.

To a solution of (5-bromo-benzofuran-2-yl)-methanol (1.6 g, 3.7 mmol) and 4-tert-butylstannanyl-pyridazine (1 g; 4.4 mmol) in 15 mL dry toluene, was added tetrakis (triphenylphosphine)palladium (0) (130 mg). The mixture was stirred at 95° C. overnight. After allowing the mixture to come to room temperature, the solution was poured into water, extracted, dried over $MgSO_4$, and filtrated to afford 2.4 g of crude product that was further purified by chromatography to afford (5-pyridazin-4-yl-benzofuran-2-yl)-methanol.

Preparation 5

2-(Biphenyl-4-yloxy)-ethanol

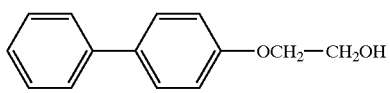

Preparation of a Compound of Formula 1 wherein $G^1$ is ($b^2$) and A is Phenyl.
Step 1
(Biphenyl-4-yloxy)-acetic acid methyl ester To a solution of 4-phenyl phenol (5.00 g, 29.38 mmol) in acetone (100 mL) was added at room temperature, methyl bromoacetate (2.92 mL, 30.84 mmol) and cesium carbonate (14.36 g, 44.06 mmol). The mixture was stirred at room temperature for 5 h. The white precipitate was filtered and the filtrate was concentrated to dryness. Purification by flash chromatography (Hex:EtOAc/7:3) gave 6.76 g of (biphenyl-4-yloxy)-acetic acid methyl ester as a white solid.
Step 2
2-(Biphenyl-4-yloxy)-ethanol To a solution of 1 (6.76 g, 27.91 mmol) in THF (50 mL) was added at room temperature lithium borohydride (1.22 g, 55.82 mmol) and the mixture was heated at reflux for 4 h. After cooling to room temperature, water was added and the product was extracted with EtOAc. The extract was washed with water, then brine, dried over sodium sulfate and concentrated to dryness. Purification by flash chromatography (dichloromethane:MeOH/99:1) gave 5.88 g of 2-(biphenyl-4-yloxy)-ethanol as a white solid.

Example 1

4-(5-Phenyl-benzofuran-2-ylmethoxycarbonylamino)-biphenyl-3-carboxylic Acid

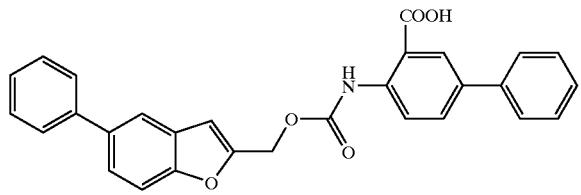

Step 1:
Methyl 2-amino-5-phenylbenzoate

To a solution of methyl 2-amino-5-bromobenzoate (2.0 g, 8.7 mmol) in dioxane (40 mL) were added phenylboronic acid (1.91 g, 15.7 mmol), potassium phosphate (4.08 g, 19.1 mmol) and tetrakis(triphenylphosphine)palladium (0.26 g, 0.22 mmol) under nitrogen. The mixture was heated at 85° C. for 20 h, then cooled to 0–5° C. Aqueous ammonium chloride was added and the mixture was extracted, washed with brine, dried ($Na_2SO_4$) and concentrated to dryness. Purification by chromatography gave 1.45 g of methyl 2-amino-5-phenylbenzoate.

Step 2:
4-(5-Phenyl-benzofuran-2-ylmethoxycarbonylamino)-biphenyl-3-carboxylic acid methyl ester To a solution of methyl 2-amino-5-phenylbenzoate (1.2 g, 5.28 mmol) in toluene (17.5 mL) and pyridine (0.75 mL, 9.24 mmol) was added 20% phosgene in toluene (3.97 mL, 7.65 mmol) under nitrogen. The mixture was heated at 90° C. for 1 h, cooled to 25° C. and filtered. The filtrate was taken to dryness. Toluene (30 mL), (5-phenyl-benzofuran-2-yl)-methanol (1.19 g, 5.28 mmol) and 4-dimethylaminopyridine (0.064 g, 0.53 mmol) were added to the residue under a nitrogen atmosphere. The mixture was heated at 50° C. for 24 h, then concentrated to dryness. Purification by chromatography followed by crystallization gave 1.04 g of 4-(5-phenyl-benzofuran-2-ylmethoxycarbonylamino)-biphenyl-3-carboxylic acid methyl ester.

Step 3:
4-(5-Phenyl-benzofuran-2-ylmethoxycarbonylamino)-biphenyl-3-carboxylic acid To a solution of 4-(5-phenyl-benzofuran-2-ylmethoxycarbonylamino)-biphenyl-3-carboxylic acid methyl ester (1.04 g, 2.17 mmol) in THF (35 mL), methyl alcohol (4.5 mL) and water (5.5 mL) was added lithium hydroxide monohydrate (0.19 g, 4.47 mmol). The mixture was stirred for 3 h, and 1N HCl was added to adjust the pH to 2. The solvents were removed in vacuo and the resulting suspension was filtered. Recrystallisation of the white crude solid gave 0.54 g of 4-(5-phenyl-benzofuran-2-ylmethoxycarbonylamino)-biphenyl-3-carboxylic acid 10, mp: 225.9–226.2° C.

Similarly following the procedure of Example 1 but replacing in Step 1 phenyl boronic acid with substituted phenylborane or other appropriate borane derivatives the following compounds were prepared:

3-(5-phenyl-benzofuran-2-ylmethoxycarbonylamino)-biphenyl-4-carboxylic acid, 11, mp: 229.5–230.0° C.;

4'-fluoro-4-(5-phenyl-benzofuran-2-ylmethoxycarbonylamino)-biphenyl-3-carboxylic acid, 12, mp: 229.4–229.6° C.;

2-(5-phenyl-benzofuran-2-ylmethoxycarbonylamino)-5-thiophen-3-yl-benzoic acid, 13 mp: 229.5–230.0° C.;

4'-fluoro-4-[5-(4-fluoro-phenyl)-benzofuran-2-ylmethoxycarbonylamino]-biphenyl-3-carboxylic acid, 14, mp: 235.1–235.7° C.;

4-[5-(4-fluoro-phenyl)-benzofuran-2-ylmethoxycarbonylamino]-biphenyl-3-carboxylic acid, 15, mp: 231.3–231.6° C.; or 2-[5-(4-fluoro-phenyl)-benzofuran-2-ylmethoxycarbonylamino]-5-pyridin-3-yl-benzoic acid, 16, mp: 225.7–229.3° C.

Similarly following the procedure of Example 1, but starting from Step 2 with the appropriate amino phenyl benzoates the following compounds were prepared:

2-(5-phenyl-benzofuran-2-ylmethoxycarbonylamino)-benzoic acid, 17, mp: 203.6–203.8° C.;

3-(5-phenyl-benzofuran-2-ylmethoxycarbonylamino)-naphthalene-2-carboxylic acid, 18, mp: 225.6–225.8° C.;

5-bromo-2-(5-phenyl-benzofuran-2-ylmethoxycarbonylamino)-benzoic acid, 19, mp: 221.2–222.0° C.;

5-methanesulfonyl-2-(5-phenyl-benzofuran-2-ylmethoxycarbonylamino)-benzoic acid, 20, mp: 234–235° C.;

5-cyano-2-(5-phenyl-benzofuran-2-ylmethoxycarbonylamino)-benzoic acid, 21, mp: 213.9–214.5° C.;

2-bromo-6-[5-(4-fluoro-phenyl)-benzofuran-2-ylmethoxycarbonylamino]-benzoic acid; 42, mp: 170.6–172° C.;

3,5-dichloro-2-[5-(4-fluoro-phenyl)-benzofuran-2-ylmethoxycarbonylamino]-benzoic acid, 22, mp: 177.7–178.5° C.;

5-fluoro-2-[5-(4-fluoro-phenyl)-benzofuran-2-ylmethoxycarbonylamino]-benzoic acid, 23, mp: 210–211.9° C.;

5-chloro-2-[5-(4-fluoro-phenyl)-benzofuran-2-ylmethoxycarbonylamino]-benzoic acid, 24, mp: 216.7–217.3° C.;

2-chloro-6-[5-(4-fluoro-phenyl)-benzofuran-2-ylmethoxycarbonylamino]-benzoic acid, 25, mp: 216.7–217.3° C.;

5-bromo-2-[5-(4-fluoro-phenyl)-benzofuran-2-ylmethoxycarbonylamino]-benzoic acid, 26, mp: 220.3–220.6° C.;

2-[5-(4-fluoro-phenyl)-benzofuran-2-ylmethoxycarbonylamino]-6-methyl-benzoic acid, 27, mp: 176.1–178.8° C.;

2-[5-(4-fluoro-phenyl)-benzofuran-2-ylmethoxycarbonylamino]-5-methyl-benzoic acid, 28, mp: 190.8–191.9° C.;

2-[5-(4-fluoro-phenyl)-benzofuran-2-ylmethoxycarbonylamino]-6-methoxy-benzoic acid, 29, mp: 160.5–164.3° C.; or 2-[5-(4-fluoro-phenyl)-benzofuran-2-ylmethoxycarbonylamino]-6-nitro-benzoic acid, 30, mp: 191.5–191.9° C.

2-cyano-6-[5-(4-fluoro-phenyl)-benzofuran-2-ylmethoxycarbonylamino]-benzoic acid, 33, mp: 150° C.-decomp.

Similarly following the procedure of Example 1, but starting from Step 2 with (2-amino-phenyl)-acetic acid ester, prepared as described in Lim, H. et al, *J. Org. Chem.* 1995, 60, 2326–2327, the following compound was prepared:

[2-(5-phenyl-benzofuran-2-ylmethoxycarbonylamino)-phenyl]-acetic acid, 42, mp: 169.5–170.9° C.

Similarly following the procedure of Example 1, but treating the appropriate benzoates with 5-thiophen-3-yl-benzofuran-2-yl)methanol the following compounds were prepared:

5-methyl-2-(5-thiophen-3-yl-benzofuran-2-ylmethoxycarbonylamino)-benzoic acid, 31, mp: 213.2–215.1° C., or 4'-fluoro-4-(2-thiophen-3-yl-benzofuran-2-ylmethoxycarbonylamino)-biphenyl-3-carboxylic acid, 32, mp: 213.2–215.1° C.

Similarly following the procedure of Example 1, but treating the appropriate benzoates with heteroaryl-benzofuran-2-yl methanols prepared as in Preparation 2,3 and 4, the following compounds were prepared:

4'-fluoro-4-(5-pyridin-3-yl-benzofuran-2-ylmethoxycarbonylamino)-biphenyl-3-carboxylic acid, 34, mp: 237.1–237.5 ° C.;

5-methyl-2-(5-pyridin-3-yl-benzofuran-2-ylmethoxycarbonylamino)-benzoic acid, 35, mp: 200.1–200.4° C.;

2-chloro-6-(5-pyridin-3-yl-benzofuran-2-ylmethoxycarbonylamino)-benzoic acid, 36, mp: 172–174° C.;

2-chloro-6-(5-pyrimidin-5-yl-benzofuran-2-ylmethoxycarbonylamino)-benzoic acid, 37, mp: 192.8–194.3° C.;

2-chloro-6-(5-pyridin-2-yl-benzofuran-2-ylmethoxycarbonylamino)-benzoic acid, 38, mp: 134.8–144.1° C.;

2-chloro-6-(5-pyrazin-2-yl-benzofuran-2-ylmethoxycarbonylamino)-benzoic acid, 39, mp: 212–214.1° C.;

2-chloro-6-(5-pyridazin-4-yl-benzofuran-2-ylmethoxycarbonylamino)-benzoic acid, 40, mp: 179–182.2° C.; or (4-bromo-2-methyl-phenyl)-carbamic acid 5-pyridin-3-yl-benzofuran-2-ylmethyl ester, 41, mp: 213.9–214.5° C.

Example 2

2-(5-Phenyl-benzofuran-2-ylmethoxycarbonylamino)-naphthalene-1-carboxylic Acid

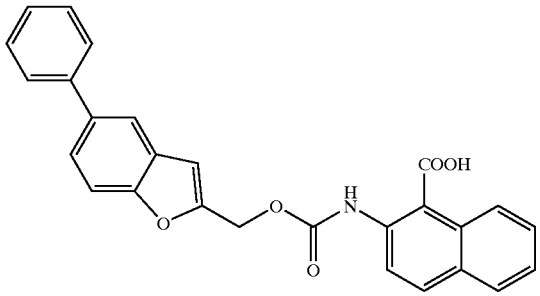

Step 1:
2-Hydroxy-naphthalene-1-carboxylic acid 2-trimethylsilanyl-ethyl ester

To a solution of 2-hydroxynaphtoic acid (2.02 g, 10.7 mmol) in dichloromethane (45 mL) and THF (2 mL) were added 2-trimethylsilylethanol (4.6 mL, 32.2 mmol) and 4-dimethylaminopyridine (1.07 g, 8.9 mmol) under $N_2$. The mixture was cooled to 0° C. and 1,3-dicyclohexylcarbodiimide (2.33 g, 11.3 mmol) was added. After removal of the ice bath, the mixture was stirred for 3 h at room temperature. 2N HCl was added to adjust the pH to 2, and the mixture was filtered to remove urea. After the separation of layers the organic phase was washed with water and brine, dried ($Na_2SO_4$), and concentrated to dryness. Purification by chromatography gave 2.92 g of 2-hydroxy-naphthalene-1-carboxylic acid 2-trimethylsilanyl-ethyl ester.

Step 2:
2-Trifluoromethanesulfonyloxy-naphthalene-1-carboxylic acid 2-trimethylsilanyl-ethyl ester To a solution of 2-hydroxy-naphthalene-1-carboxylic acid 2-trimethylsilanyl-ethyl ester (2.92 g, 10.1 mmol) in pyridine (7 mL) was added trifluoromethanesulfonic anhydride (1.91 mL, 11.3 mmol) at 0–5° C. under an argon atmosphere. After removal of the ice bath the mixture was stirred for 3 h at room temperature. The mixture was diluted with EtOAc and washed with 2N HCl, 10% $NaHCO_3$, dried ($Na_2SO_4$), and concentrated to dryness. Purification by chromatography gave 4.22 g of 2-trifluoromethanesulfonyloxy-naphthalene-1-carboxylic acid 2-trimethylsilanyl-ethyl ester.

Step 3:
2-Amino-naphthalene-1-carboxylic acid 2-trimethylsilanyl-ethyl ester

To a solution of 2-trifluoromethanesulfonyloxy-naphthalene-1-carboxylic acid 2-trimethylsilanyl-ethyl ester (4.22 g, 10.0 mmol) in THF (40 mL) were added cesium carbonate (4.58 g, 14.05 mmol), palladium acetate (0.067 g, 0.3 mmol), BINAP (0.28 g, 0.45 mmol) and benzophenone imine (2.0 mL, 12.04 mmol) under an argon atmosphere. The mixture was heated at 65° C. for 16 h. After addition of water the mixture was extracted with EtOAc, washed with brine, dried ($Na_2SO_4$) and concentrated to dryness. To the residue were added THF (40 mL), methyl alcohol (10 mL) and 2N HCl (6.6 mL), and the mixture was stirred for 2 h at room temperature. After addition of 10% $NaHCO_3$ the mixture was extracted, dried ($Na_2SO_4$) and concentrated to dryness. Purification by chromatography gave 1.8 g of 2-amino-naphthalene-1-carboxylic acid 2-trimethylsilanyl-ethyl ester.

Step 4:
2-(5-Phenyl-benzofuran-2-ylmethoxycarbonylamino)-naphthalene-1-carboxylic acid 2-trimethylsilanyl-ethyl ester To a solution of 2-amino-naphthalene-1-carboxylic acid 2-trimethylsilanyl-ethyl ester (604 mg, 2.1 mmol) in toluene (12 mL) were added pyridine (0.34 mL, 4.21 mmol) and 20% phosgene in toluene (1.58 mL, 3.04 mmol) under a nitrogen atmosphere. The mixture was heated at 90° C. for 1.5 h, cooled to room temperature and filtered. The filtrate was concentrated to dryness. To the residue were added toluene (12 mL), (5-phenyl-benzofuran-2-yl)-methanol (471 mg, 2.10 mmol) and 4-dimethylaminopyridine (26 mg, 0.21 mmol) under a nitrogen atmosphere, and the mixture was heated at 90° C. for 16 h. Following dilution with EtOAc, the mixture was washed with 2N HCl, 10% $NaHCO_3$, and brine, dried ($Na_2SO_4$) and concentrated to dryness. Purification by chromatography gave 582 mg of 2-(5-phenyl-benzofuran-2-ylmethoxycarbonylamino)-naphthalene-1-carboxylic acid 2-trimethylsilanyl-ethyl ester.

Step 5:
2-(5-Phenyl-benzofuran-2-ylmethoxycarbonylamino)-naphthalene-1-carboxylic acid To a solution of 2-(5-phenyl-benzofuran-2-ylmethoxycarbonylamino)-naphthalene-1-carboxylic acid 2-trimethylsilanyl-ethyl ester (574 mg, 1.07 mmol) in DMF (5 mL) was added 1.0M tetra-n-butylammonium fluoride (1.1 mL, 1.07 mmol) under a nitrogen atmosphere. The mixture was stirred for 1.5 h. Water was added and the mixture was extracted, washed with water and brine, dried and concentrated to ca. 3 mL. The suspension was cooled at 0–5° C. for 40 min and filtered. Recrystallization of the obtained white solid gave 224 mg of 2-(5-phenylbenzofuran-2-ylmethoxycarbonylamino)-naphthalene-1-carboxylic acid, 201, mp: 174.5–177.2° C.

Similarly, 2-[5-(4-fluoro-phenyl)-benzofuran-2-ylmethoxycarbonylamino]-naphthalene-1-carboxylic acid 202, mp: 204.5–205° C., was prepared.

Example 3

2-[5-(4-Fluoro-phenyl)-benzofuran-2-ylmethoxycarbonylamino]-5-isopropoxy-benzoic Acid

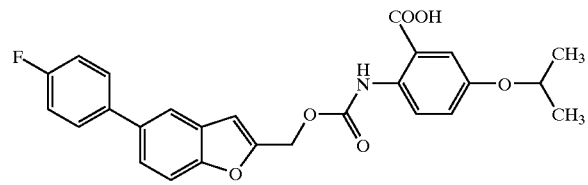

Step 1:
5-Isopropoxy-2-nitro-benzoic acid

60% NaH in oil (950 mg, 23.8 mmol) was added to isopropyl alcohol (4.1 mL) in THF (20 mL) under a nitrogen atmosphere. After stirring for 30 min, 5-fluoro-2-nitrobenzoic acid (2.0 g, 10.8 mmol) was added, and the mixture was heated at reflux for 6 h. Following addition of 2N HCl to adjust the pH to 2, the mixture was extracted, washed with brine, dried (Na₂SO₄) and concentrated to dryness. Purification by chromatography gave 950 mg of 5-isopropoxy-2-nitro-benzoic acid.

Step 2:
5-Isopropoxy-2-amino-benzoic acid

To a solution of 5-isopropoxy-2-nitro-benzoic acid (946 mg, 4.2 mmol) in THF (15 mL) was added 5% Pd/C (95 mg) under a nitrogen atmosphere. A balloon filled with H₂ was set up. The mixture was stirred for 3.5 h and filtered. The filtrate was dried to yield 816 mg of 5-isopropoxy-2-amino-benzoic acid.

Step 3:
5-Isopropoxy-2-amino-benzoic acid methyl ester

To a solution of 5-isopropoxy-2-amino-benzoic acid (806 mg) in DMF (10 mL) was added 60% in oil NaH (182 mg, 4.53 mmol) at 0–5° C. under an argon atmosphere. The ice bath was removed and the mixture was stirred for 40 min at room temperature. After addition of methyl iodide (0.33 mL, 5.45 mmol) the mixture was stirred at room temperature for an additional 6 h. 10% KHSO₄/Na₂SO₄ was added and the mixture was extracted, washed with brine, dried (Na₂SO₄), and concentrated to dryness. Purification by chromatography gave 114 mg of 5-isopropoxy-2-amino-benzoic acid methyl ester.

Step 4:
2-[5-(4-Fluoro-phenyl)-benzofuran-2-ylmethoxycarbonylamino]-5-isopropoxy-benzoic acid Following Steps 2 and 3 of Example 1, 5-isopropoxy-2-amino-benzoic acid methyl ester was reacted with (5-phenyl-benzofuran-2-yl)-methanol and the resulting ester was hydrolized to yield 2-[5-(4-fluoro-phenyl)-benzofuran-2-ylmethoxycarbonylamino]-5-isopropoxy-benzoic acid 301, mp: 195–196.5° C.

Example 4

5-(5-Phenyl-benzofuran-2-ylmethoxycarbonylamino)-biphenyl-3-carboxylic Acid

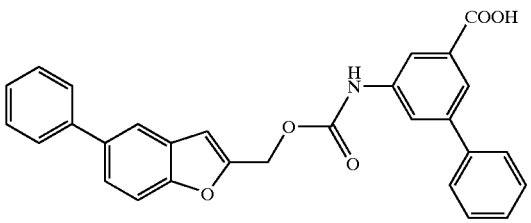

Step 1:
3-Iodo-5-nitro-benzoic acid

To a suspension of 3-amino-5-nitrobenzoic acid (5.0 g, 27.45 mmol) in water (23 mL) and conc. sulfuric acid (3.15 mL) was added at 0–5° C. sodium nitrite (1.89 g, 27.45 mmol), the mixture was stirred at this temp for 1 h, and potassium iodide (7.59 g, 45.75 mmol) was added. After stirring at room temperature for an additional 2 h, the mixture was extracted, washed with a 10% solution of sodium sulfite, followed by water, then brine, dried over magnesium sulfate, and concentrated to dryness. Purification by flash chromatography gave 5.88 g of 3-iodo-5-nitro-benzoic acid as a yellow solid.

Step 2:
3-Iodo-5-nitro-benzoic acid methyl ester

To a solution of 3-iodo-5-nitro-benzoic acid (5.88 g, 20.07 mmol) in dichloromethane (60 mL) at room temperature under nitrogen was added oxalyl chloride (1.92 mL, 24.28 mmol) and a drop of DMF. The mixture was stirred for 1 h. methanol (20 mL), DMAP (0.245 g, 2.00 mmol), and triethylamine (3.08 mL, 24.28 mmol) were added and the mixture was stirred for an additional 2 h. Water was added and the product was extracted, washed with water, then brine, dried over magnesium sulfate and concentrated to dryness. Purification by chromatography gave 6.04 g of 3-iodo-5-nitro-benzoic acid methyl ester, as a yellow solid.

Step 3:
5-Nitro-biphenyl-3-carboxylic acid methyl ester

Phenylboronic acid (2.14 g, 17.59 mmol), potassium phosphate (4.50 g, 21.20 mmol), tetrakis(triphenylphosphine)palladium(0) (0.283 g, 0.24 mmol) and 3-iodo-5-nitro-benzoic acid methyl ester (3.00 g, 9.77 mmol) in dioxane (30 mL) were heated at 80° C. for 3 h. Saturated ammonium chloride was added and the product was extracted, washed with water, brine, dried over magnesium sulfate, and concentrated to dryness. Purification by chromatography gave 1.85 g of 5-nitro-biphenyl-3-carboxylic acid methyl ester, as a white solid.

Step 4:
5-Amino-biphenyl-3-carboxylic acid methyl ester

5-Nitro-biphenyl-3-carboxylic acid methyl ester (1.85 g, 7.19 mmol) and 10% Pd/C (0.185 g) in EtOAc (20 mL) were hydrogenated under balloon for 2 h. The catalyst was filtered and the filtrate was concentrated to dryness. The crude 5-amino-biphenyl-3-carboxylic acid methyl ester was a yellow solid and was taken to the next step.

Step 5:
5-(5-Phenyl-benzofuran-2-ylmethoxycarbonylamino)-biphenyl-3-carboxylic acid methyl ester To a solution of 5-amino-biphenyl-3-carboxylic acid methyl ester (crude from Step 4; 1.00 g, 4.40 mmol) and pyridine (0.711 mL, 8.80 mmol) in toluene (15 mL) at room temperature under argon was added 20% phosgene in toluene (3.3 mL, 6.3 mmol) and the mixture was heated at 90° C. for 1 h. The mixture was filtered, and the filtrate was concentrated to dryness (0.373 g). The crude material was dissolved in toluene (4 mL), (5-phenyl-benzofuran-2-yl)-methanol (0.300 g, 1.38 mmol) and DMAP (0.016 g, 0.137 mmol) were added and the mixture was heated at 90° C. for 18 h. The solvent was evaporated to dryness. Purification by flash chromatography gave 0.125 g of a white solid.

Step 6:
5-(5-Phenyl-benzofuran-2-ylmethoxycarbonylamino)-biphenyl-3-carboxylic acid To a solution of 5-(5-phenyl-benzofuran-2-ylmethoxycarbonylamino)-biphenyl-3-carboxylic acid methyl ester (0.125 g, 0.2618 mmol) in THF (2 mL) was added at room temperature 1.0 M LiOH and the mixture was stirred for 3 h. The solvent was evaporated, water was added, followed by 2N HCl to adjust the pH to 1–2, and the product was extracted, washed with water, then brine, and dried over magnesium sulfate and concentrated to dryness. Purification by crystallization gave 0.040 g of 5-(5-phenyl-benzofuran-2-ylmethoxycarbonylamino)-biphenyl-3-carboxylic acid 401 as a white solid, mp: 235.7–238.9° C.

Similarly following steps 2 to 6, 4-(5-phenyl-benzofuran-2-ylmethoxycarbonylamino)-biphenyl-2-carboxylic acid, 402, mp: 174.1–174.7° C.; was prepared from the commercially available 2-bromo-5-nitrobenzoic acid.

Similarly following steps 4 to 6, 3-(5-phenyl-benzofuran-2-ylmethoxycarbonylamino)-benzoic acid, 403, mp: 250.7–251° C., was prepared from 3-nitrobenzoic acid.

Example 5

3-(1H-Tetrazol-5-yl)-biphenyl-4-yl-carbamic Acid 5-phenyl-benzofuran-2-ylmethyl ester

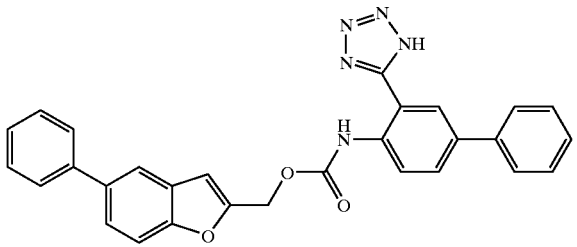

Step 1:
4-Amino-biphenyl-3-carbonitrile

A mixture of 2-amino-5-bromo-benzonitrile (4.0 g, 0.0203 mole) in 55 mL of dioxane was treated with sodium carbonate (7.1 g) in 55 mL of water, phenyl boronic acid (2.72 g, 0.0223 mole), and tetrakistriphenylphosphine palladium (0) (0.235 g). the mixture was heated to 100° C. with stirring under an atmosphere of argon for 3 h., cooled to room temperature, poured into ethyl acetate, washed with 1M HCl, then brine, dried, evaporated and purified by chromatography to give 2.91 g of 4-amino-biphenyl-3-carbonitrile as a yellow solid.

Step 2:
3-Cyano-biphenyl-4-yl)-carbamic acid-5-phenyl-benzofuran-2-yl-methyl ester To a solution of 4-amino-biphenyl-3-carbonitrile (1.2 g, 6.33 mmol) and pyridine (2 mL, 25.3 mmol) was added 20% phosgene in toluene (5.7 mL(10.8 mmol) and the mixture was heated at 90° C. for 2 hrs. The mixture was filtered and the filtrate was concentrated to dryness. The crude material was dissolved in THF, and (5-phenyl-benzofuran-2-yl)-methanol (0.52 g, 2.3 mmol) and triethylamine (0.70 g, 6.9 mmol) were added. The mixture was heated at 50° C. for 15 h. The solvent was evaporated to dryness. Purification by chromatography gave 0.78 g of 3-cyano-biphenyl-4-yl)-carbamic acid-5-phenyl-benzofuran-2-yl-methyl ester as a light yellow solid.

Step 3:
3-(1H-Tetrazol-5-yl)-biphenyl-4-yl]-carbamic acid 5-phenyl-benzofuran-2-yl-methyl ester A mixture of (3-cyano-biphenyl-4-yl)-carbamic acid-5-phenyl-benzofuran-2-yl-methylester (0.40 g, 0.90 mmol), sodium azide (0.117 g, 1.80 mmol) and ammonium chloride (0.096 g, 1.80 mmol) in 3 mL DMF was heated to 90° C. under a nitrogen atmosphere for 20 h. The mixture was cooled to room temperature, ethyl acetate was added and the solution was washed with 1M HCl, followed by water, dried and concentrated to dryness. Purification by chromatography gave 72 mg of 3-(1H-tetrazol-5-yl)-biphenyl-4-yl]-carbamic acid 5-phenyl-benzofuran-2-ylmethyl ester 501, mp: 180–183° C.

Similarly following the procedure of Example 5, but replacing in Step 1 benzene boronic acid with the appropriate substituted benzene boronic acid derivatives, and/or replacing (5-phenyl-benzofuran-2-yl)-methanol in Step 2 with the appropriate 2-hydroxymethyl-benzofuran derivatives the following compounds were prepared:

[3-(1H-tetrazol-5-yl)-biphenyl-4-yl]-carbamic acid 5-(3,5-dichloro-phenyl)-benzofuran-2-ylmethyl ester 502, mp: 127.50–134° C.;

[4'-fluoro-3-(1H-tetrazol-5-yl)-biphenyl-4-yl]-carbamic acid 5-(4-fluoro-phenyl)-benzofuran-2-ylmethyl ester 505, mp: 209–211° C.; or

[3-(1H-tetrazol-5-yl)-biphenyl-4-yl]-carbamic acid 5-(4-fluoro-phenyl)-benzofuran-2-ylmethyl ester 509, mp: 192–230° C.

Similarly following the procedure of Example 5, but starting from Step 2 with 2-amino-benzonitrile derivatives, reacting with the appropriate 2-hydroxymethyl-benzofuran derivatives, and treating the carbonitrile group with sodium azide to form the tetrazolyl substitutent as in Step 3, the following compounds were prepared:

[2-(1H-tetrazol-5-yl)-phenyl]-carbamic acid 5-(4-fluoro-phenyl)-benzofuran-2-ylmethyl ester 503, mp: 155–158° C.;

[4-bromo-2-(1H-tetrazol-5-yl)-phenyl]-carbamic acid 5-(4-fluoro-phenyl)-benzofuran-2-ylmethyl ester 504, mp: 121–138° C.;

[4-fluoro-2-(1H-tetrazol-5-yl)-phenyl]-carbamic acid 5-(4-fluoro-phenyl)-benzofuran-2-ylmethyl ester, 506, mp: 121–125.2° C.;

[4-bromo-2-(1H-tetrazol-5-yl)-phenyl]-carbamic acid 5-phenyl-benzofuran-2-ylmethyl ester, 507, mp: 166–190° C.; or

[2-(1H-tetrazol-5-yl)-phenyl]-carbamic acid 5-phenyl-benzofuran-2-ylmethyl ester, 508, mp: 213–216.5° C.

Example 6

4-(Biphenyl-4-ylmethoxycarbonylamino)-biphenyl-3-carboxylic Acid

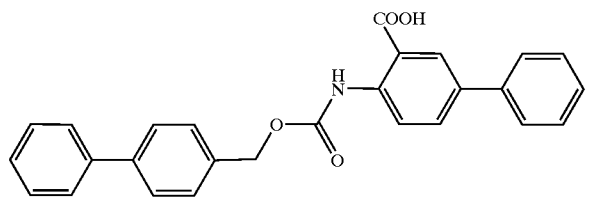

To a solution of methyl-5-phenyl-2-aminobenzoate (0.40 g, 1.76 mmol) and pyridine (0.285 mL, 3.52 mmol) in toluene (7 mL) at room temperature under argon was added 20% phosgene in toluene (1.32 mL, 2.55 mmol) and the mixture was heated at 90° C. for 1 h. The mixture was filtered, and the filtrate was concentrated to dryness. The crude material was dissolved in toluene (10 mL), biphenyl-4-methanol (0.270 g, 1.46 mmol) and DMAP (0.018 g, 0.146 mmol) were added and the mixture was heated at 90° C. for 18 h. The solvent was evaporated to dryness to give 0.51 g of 4-(biphenyl-4-ylmethoxycarbonylamino)-biphenyl-3-carboxylic acid methyl ester.

To a solution of 4-(biphenyl-4-ylmethoxycarbonylamino)-biphenyl-3-carboxylic acid methyl ester (0.51 g, 1.179 mmol) in THF (5 mL) was added at room temperature 1.0 M LiOH (2.42 mL, 2.42 mmol) and the mixture was stirred for 3 h. The solvent was evaporated, water was added, followed by 2N HCl to adjust the pH to 1–2, and the product was extracted with ethyl acetate. The extract was washed with water, then brine, and dried over magnesium sulfate, concentrated to dryness and purified by chromatography to yield 0.317 g of 4-(biphenyl-4-ylmethoxycarbonylamino)-biphenyl-3-carboxylic acid 601, mp: 234.5–235.6° C.

Example 7

2-Amino-6-[5-(4-fluoro-phenyl)-benzofuran-2-ylmethoxycarbonylamino]-benzoic acid

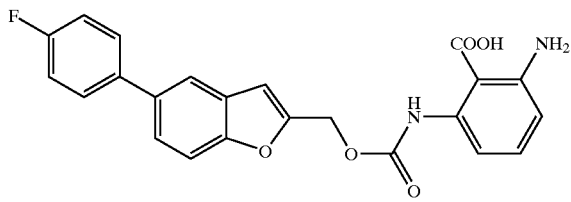

Step 1:
(3-Oxo-1,3-dihydrobenzo[c]isoxazol-4-yl)carbamic acid 5-(4-fluorophenyl) benzofuran-2-ylmethyl ester.

To a solution of 2-[5-(4-fluorophenyl)benzofuran-2-ylmethoxycarbonylamino]-6-nitrobenzoic acid methyl ester (348 mg, 0.75 mmol) in EtOH (50 mL) at room temperature was added $SnCl_2 \cdot 2H_2O$ (677 mg, 3.0 mmol) and the mixture was allowed to stir overnight. The mixture was diluted with $H_2O$ and then concentrated in vacuo. The aqueous residue was neutralized with 1N NaOH and extracted with $CH_2Cl_2$. The organic extracts were dried over anhydrous $Na_2SO_4$ and concentrated en vacuo to give 192 mg (61.15%) of (3-oxo-1,3-dihydrobenzo[c]isoxazol-4-yl)carbamic acid 5-(4-fluorophenyl) benzofuran-2-ylmethyl ester as a tan powder, mp: 160.5–161.5° C. Anal. Calcd for $C_{23}H_{15}FN_2O_5$: C, 66.03; H, 3.61; N, 6.70. Found: C, 65.59; H, 3.56; N, 6.69.

Step 2
2-Amino-6-[5-(4-fluorophenyl)benzofuran-2-ylmethoxycarbonylamino]benzoic acid.

(3-Oxo-1,3-dihydrobenzo[c]isoxazol-4-yl)carbamic acid 5-(4-fluorophenyl)benzofuran-2-ylmethyl ester (70 mg, 0.17 mmol) was dissolved in 2M $H_2SO_4$ at room temperature. Zinc dust was added and the mixture was stirred at 80° C. for 4 hours. Upon cooling, the mixture was filtered. The filtrate was neutralized with diluted NaOH and extracted with $CH_2Cl_2$. The organic extracts were dried over anhydrous $Na_2SO_4$ and concentrated en vacuo to give 23 mg (32.86%) of 2-amino-6-[5-(4-fluorophenyl)benzofuran-2-ylmethoxycarbonylamino]benzoic acid 701, as a tan powder: mp: 176.4–178.5° C. Anal Calcd for $C_{23}H_{17}FN_2O_5$: C, 65.71; H, 4.08; N, 6.66. Found: C, 66.71; H, 4.56; N, 5.95.

Example 8

2-[2-(Biphenyl-4-yloxy)-ethoxycarbonylamino]-6-chloro-benzoic Acid

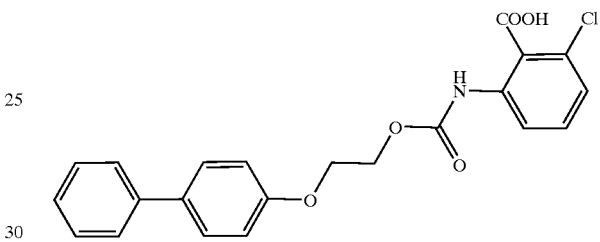

Step 1
2-[2-(Biphenyl-4-yloxy)-ethoxycarbonylamino]-6-chlorobenzoic acid 2-trimethylsilanyl-ethyl ester Following the procedure described herein in Example 1 Step 2, to a solution of 2-(trimethylsilyl)ethyl 2-amino-5-chlorobenzoate (200 mg, 0.736 mmol), pyridine (0.12 mL, 1.47 mmol) was added 20% phosgene in toluene (0.57 mL, 1.1 mmol) in toluene (5 mL) and the mixture was heated at 90° C. for 1 h. The mixture was filtered and the filtrate was concentrated to dryness. The crude material was dissolved in toluene (5 mL) and 2-(biphenyl-4-yloxy)-ethanol prepared as described in preparation 5 (158 mg, 0.736 mmol) and DMAP (9 mg, 0.074 mmol) were added. The mixture was heated at 90° C. for 18 h, and the solvent evaporated to dryness to give 340 mg 2-[2-(biphenyl-4-yloxy)-ethoxycarbonylamino]-6-chloro-benzoic acid 2-trimethylsilanyl-ethyl ester as a white solid.

Step 2
2-[2-(Biphenyl-4-yloxy)-ethoxycarbonylamino]-6-chlorobenzoic acid

To a solution of 2-[2-(biphenyl-4-yloxy)-ethoxycarbonylamino]-6-chloro-benzoic acid 2-trimethylsilanyl-ethyl ester (340 mg, 0.664 mmol) and 1.0M tetrabutyl ammonium fluoride in THF (0.66 mL, 0.6636 mmol) in DMF (6 mL) and the mixture was stirred for 2 h. 2N HCl was added to adjust the pH to 1–2 and the mixture was partitioned between water and ethyl acetate. The combined organics were washed with water, then brine dried over magnesium sulfate and concentrated to dryness. Purification by crystallization gave 0.121 g of 2-[2-(biphenyl-4-yloxy)-ethoxycarbonylamino]-6-chloro-benzoic acid as a white solid, 801, mp:157.5–158.9.

Similarly, replacing 2-(trimethylsilyl)ethyl 2-amino-5-chlorobenzoate in step 3 with 2-(trimethylsilyl)ethyl 2-amino-4-methylbenzoate, the following compound was prepared:

2-[2-(biphenyl-4-yloxy)-ethoxycarbonylamino]-5-methyl-benzoic acid, 802, mp: 175.5–177.8.

In a similar manner, 2-chloro-6-[2-(4-pyrimidin-5-yl-phenoxy)-ethoxycarbonylamino]-benzoic acid 803, mp: 194.8–198.9, was prepared replacing 2-biphenyl-4-yloxy-ethanol in step 1 with commercially available, 2-(4-bromophenoxy)ethanol, followed with condensation with 5-pyridiminyl boronic acid and tetrakis(triphenylphosphine) palladium under conditions similar to those described in preparation 1, step 2.

Example 9

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Example 10

Composition for Oral Administration

| Ingredient | % wt./wt. |
| --- | --- |
| Active ingredient | 20.0% |
| Magnesium stearate | 0.5% |
| Crosscaramellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Example 11

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

The ingredients are mixed to form a suspension for oral administration.

Example 12

Parenteral Formulation (IV)

| Ingredient | % wt./wt. |
| --- | --- |
| Active ingredient | 0.25 g |
| Sodium Chloride | Qs to make isotonic |
| Water for injection to | 100 mL |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Example 13

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example 14

Topical Formulation

| Ingredients | grams |
| --- | --- |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Example 15

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 16

In vitro Human Platelet IP Receptor Radioligand Binding Assay

The in vitro Human Platelet IP Receptor Binding Assay measured the strength of a potential drug's binding affinity to its intended target.

For each drug tested, the concentration producing 50% inhibition of binding ($IC_{50}$) and Hill slope was determined using iterative curve fitting techniques. If a radioligand Kd was known the inhibition dissociation constant (Ki) of each drug was determined according to the method of Cheng & Prusoff (1973). For this receptor, a typical Kd using the preceding experimental conditions was 1 E-8 M. Usually the negative logarithm of the Ki ($pK_i$) was presented.

EXPERIMENTAL DESIGN
The following buffers were prepared using the purest available water.

| | |
|---|---|
| Lysis Buffer: 10 mM Tris-HCl, 1.0 mM EDTA (di-Na) | pH 7.5 @ 4° C. |
| Assay Buffer: 20 mM Tris-HCl, 5.0 mM MgCl$_2$ | pH 7.4 @ 25° C. |
| Wash Buffer: 20 mM Tris-HCl, 5.0 mM MgCl$_2$ | pH 7.4 @ 4° C. |

1. Membrane Preparation 250 mL Platelet Rich Plasma was transferred into 250 mL centrifuge tubes and spun at 6000 g for 10 min. at 20° C. Pellets were then resuspended in IP lysis buffer and homogenized using a polytron(setting 7, 1×20 sec. burst), brought up to a final volume of 180 mL and centrifuged at 40,000 g for 15 min. at 4° C. The pellets were then resuspended in IP assay buffer, protein density determined by BCA method (Pierce) and stored in 2.0 mL vials at −80° C. for subsequent assay use.

To obtain at least 80% specific binding, 50 µg protein/assay tube was used in a competition experiment. The final radioligand concentration was 1 to 3E-8 M.

2. Competition Assay

The membranes were thawed at room temperature and then diluted in assay buffer to the appropriate concentration.
First buffer, drug, radioligand, and lastly, membranes were added to the assay tubes.
The assay tubes were incubated at 25° C. for 60 min.
The assay tubes were filtered onto 0.3% PEI pre-treated glass fiber filtermats (GF/B) using Packard Top Count 96 well cell harvester. The tubes were rinsed three times with ice cold 20 mM Tris-HCl, 5 mM MgCl$_2$, pH=7.4 (3×0.5 mL/sample).
Bound radioactivity was determined using liquid scintillation counting.

Compounds of this invention were active in this assay.

Example 17

Carrageenan-Induced Mechanical Hyperalgesia Assay

The anti-inflammatory/analgesic activity of compounds of this invention was determined by the Carrageenan-Induced Mechanical Hyperalgesia Assay by measuring the inhibition of carrageenan-induced paw hyperalgesia in the rat, using a modification of the method described in L. O. Randall and J. J. Selitto, *Archives of International Pharmacodynamics*, 1957, 11, 409–419, and Vinegar et al., *Journal of Pharmacology and Experimental Therapeutics*, 1969, 166, 96–103.

Male Sprague-Dawley rats (130–150 g) were weighed and randomly assigned to treatment groups (n=10). To induce mechanical hyperalgesia, rats were lightly anesthetized with halothane and administered 1% carrageenan or vehicle 1 (100 µl) in the plantar surface of the left hindpaw. Rats were administered vehicle (10 mL/kg, p.o. or 1 mL/kg, i.v.) or compounds of this invention (at 1, 3, 10, 30 and 100 mg/kg, p.o.) or (0.3, 1.0, 3.0 and 10 mg/kg, i.v.) one hour before testing. Mechanical hyperalgesia was measured using an Analgesy-meter (UGO BASILE, Biological Research Apparatus, Comerio, Italy). The vehicle- or carrageenan-treated hindpaw was placed on the dome of the apparatus, plantar surface facing down. A constantly increasing force was then applied to the dorsal surface of the paw. The force at which the rat withdrew its paw, struggled, or vocalized was considered the end point.

Treatment groups were compared using a one-way analysis of variance on the paw withdrawal force (RESP). Pairwise comparisons for the drug-treated groups to the vehicle group were made using Fisher's LSD strategy and Dunn's procedure. Percent inhibition of mechanical hyperalgesia was calculated for each animal, and the average $ID_{50}$ value was estimated using the following sigmoidal model:

$$\% \text{ inhibition} = 100/(1+\exp((ID_{50}-\text{dose})/N))$$

where $ID_{50}$ is the dose of the compound needed to inhibit half of the maximum response (i.e., 100% in this model) and N is a curvature parameter.

The compounds of this invention were active in this assay.

Example 18

Complete Freund's Adjuvant-Induced Mechanical Hyperalgesia Assay

The anti-inflammatory/analgesic activity of compounds of this invention may also be determined using an adjuvant-induced arthritis pain model in the rat, where pain is assessed by the animal's response to the squeezing of the inflamed foot, using a modification of the method described in J. Hylden et al., *Pain* 1989, 37, 229–243. The modification includes the assessment of hyperalgesia instead of changes in activity of spinal cord neurons.

Briefly, rats were weighed and randomly assigned to treatment groups. To induce mechanical hyperalgesia, rats were lightly anesthetized with halothane and 100 µl of Complete Freund's Adjuvant or saline was administered into the plantar surface of the left hindpaw. Twenty-four hours later, water (vehicle) or compounds of this invention were orally administered to the rats one hour before testing. Mechanical hyperalgesia was measured using an Analgesy-meter (UGO BASILE, Biological Research Apparatus, Comerio, Italy). The saline or carrageenan-treated hindpaw was placed on the dome of the apparatus, plantar surface facing down. A constantly increasing force was then applied to the dorsal surface of the paw, and the force at which the rat withdrew its paw, struggled, or vocalized was considered the end point. The treatment groups were compared using a one-way analysis of variance on the paw withdrawal force. Percent inhibition was calculated for each animal in the form:

$$100 \times ((c/d-c/v)+(s/v-c/v))$$

where c/d is the paw withdrawal force for the carrageenan-treated paw in an animal to which drug has been administered; c/v is the paw withdrawal force for the carrageenan-treated paw in an animal to which vehicle has been administered; and s/v is the paw withdrawal force for the saline-treated paw in an animal to which vehicle has been administered. Significance was determined using Student's t-test.

The compounds of the invention were active in this assay.

Example 19

Inhibition of Bladder Contractions Induced by Isovolumetric Bladder Distension in Rats The inhibition of bladder contractions was determined by an assay using a modification of the method described in C. A. Maggi et al., *J. Pharm. and Exper. Therapeutics*, 1984, 230, 500–513.

Briefly, male Sprague-Dawley rats (200–250 g) were weighed and randomly assigned to treatment groups. A catheter was inserted through the urethra into the bladder to induce bladder contractions, and a warm saline solution (5 mL) was infused. Rhythmic contractions were produced in about 30% of the animals. The compounds of the invention (0.1, 0.3 or 1 mg/kg) were administered intravenous at the onset of regular rhythmic contractions. The effects on rhythmic contracts were then measured.

The compounds of this invention were active in this assay.

Example 20

Inhibition of Volume-Induced Contractions in Rats

The inhibition of bladder contractions was determined by an assay using a modification of the method described in S. S. Hegde et al., *Proceedings of the 26th Annual Meeting of the International Continence Society* (August 27th–30th) 1996, Abstract 126.

Female Sprague-Dawley rats were anesthetized with urethane and instrumented for intravenous administration of drugs and, in some cases, measurement of arterial pressure, heart rate and intra-bladder pressure. The effect of test compounds on volume-induced bladder contractions was determined in separate groups of animals. Volume-induced reflex bladder contractions were induced by filling the bladder with saline. The test compounds were administered intravenously in a cumulative manner at 10-minute intervals. Atropine (0.3 mg/kg, iv) was administered at the end of the study as a positive control.

The compounds of this invention were active in this assay.

Example 21

Reversal of Endotoxin-Induced Hypotension in Rats

Septic shock, sometimes referred to as endotoxic shock, is caused by the presence of infectious agents, particularly bacterial endotoxins, in the bloodstream and is characterized by hypotension and organ dysfunction. Many symptoms of septic shock, in particular, hypotension, are induced in the rat by the administration of bacterial endotoxins. The ability of a compound to inhibit endotoxin-induced hypotension is therefore predictive of the utility of the compound in the treatment of septic or endotoxic shock.

The activity of the compounds of the invention in the treatment of septic or endotoxic shock was determined by measuring the reversal of endotoxin-induced hypotension in the rat, using a modification of the method described in M. Giral et al., *British Journal of Pharmacology*, 1969, 118, 1223–1231.

Briefly, adult rats (>200 g) were anesthetized with an inhalation anesthetic and femoral arteries and veins were cannulated for insertion of blood pressure transducers and drug administration lines, respectively. They were placed in Mayo restrainers while still under the influence of the anesthetic. After recovery from anesthesia and stabilization of heart rate and blood pressure (which typically required about 30 minutes), endotoxin (50 mg/kg *E. coli* and 25 mg/kg *Salmonella*) was administered intravenously. Changes in blood pressure and heart rate were monitored. After one hour, compounds of this invention or vehicle were also administered intravenously, and cardiovascular parameters were continuously monitored for the next three hours. Responses are represented as percentage return to initial diastolic blood pressure. Significance was determined using Student's t-test.

The compounds of this invention were active in this assay.

Example 22

Carbaprostacyclin Induced Writhing Test

The analgesic properties of these compounds was investigated with the carbaprostacyclin induced writhing test. The rats (100–130 g) are weighed and randomly assigned to treatment groups (n=8). Each animal is administered vehicle, reference substance or test substance at a dose and dose volume determined by the study director. At the appropriate time after drug dose (peak time of action for test compound), carbaprostacyclin (30 $\mu$g/kg, 2 mL/kg, i.p.) is administered. Following carbaprostacyclin administration, the rats are placed in individual plexiglas cages. Writhes are counted for 15 minutes beginning 5 minutes following carbaprostacyclin administration. A writhe consists of a dorsiflexion or strong contraction of the abdominal musculature with simultaneous stretching.

Group comparisons: The treatment groups and the negative control (vehicle+the inducing agent) are compared using a one-way analysis of variance. Pairwise comparisons between the negative control and each treatment group are made using Fisher's LSD test with Bonferroni's adjustment if the overall difference is not significant. The ranked data are applied in the analysis. The positive control group is compared to the negative control group using Wilcoxon rank-sum test for assay verification.

Estimation of $ID_{50}$: The % inhibition is calculated for each animal in the form of $100*(1-(\text{number of writhes/mean writhes for the vehicle group}))$. The $ID_{50}$ is estimated using the following sigmoidal model: % inhibition=$100/(1+(ID_{50}/\text{dose})^N)$, where $ID_{50}$ is the dose for the compound to achieve half of the maximum response (50%) in the dose response curve, N is the curvature parameter. The maximum response is assumed 100% in the model.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula Formula (I):

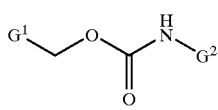

wherein:

G¹ is-a group of formula a

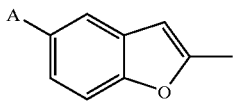

A is selected from the group phenyl, pyridinyl, pyrimidinyl, pyridazinyl, pyrazinyl, and thienyl, all optionally substituted with lower alkyl, halogen, haloalkyl, alkoxy, cyano, nitro, —SO₂R', —NSO₂R', —SO₂NR'R", —NR'R", or —COR'; R' and R" are each independently hydrogen or lower alkyl;

G² is selected from the group represented by the Formula c, d, e, and f

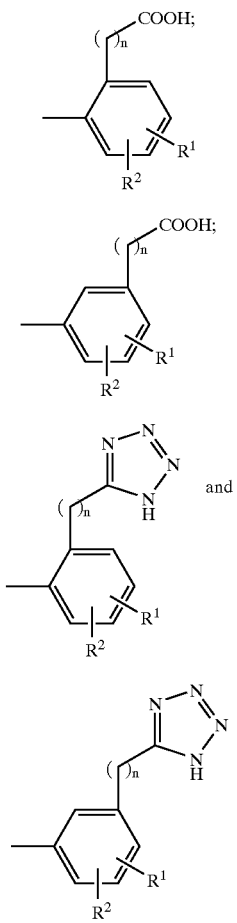

R¹ and R² are independently in each occurrence selected from the group consisting of hydrogen, lower alkyl, halogen, haloalkyl, —NR'R", —OR', —NR'SO₂R", —SO₂R', —COR', cyano, nitro, phe-nyl (optionally substituted with halo, alkyl, cyano, nitro, or alkoxy), or heteroaryl (optionally substituted with halo, alkyl, cyano, nitro or alkoxy), said heteroaryl having one to three rings, of four to eight atoms per ring, incorporating within each ring one of two heteroatoms chosen from nitrogen, oxygen or sulfur; and wherein R' and R" are as defined hereinbefore;

R¹ and R², if adjacent, taken together with the carbons to which they are attached may also form an aromatic ring, optionally substituted with one or two substitutents selected from the group consisting of lower alkyl, halo, cyano, or lower alkoxy;

n is an integer selected from 0, 1, 2 and 3;

or pharmaceutically acceptable salts or solvates thereof.

2. The compound of claim 1, wherein G² is selected from the group represented by the Formula c and d.

3. The compound of claim 1, wherein G² is selected from the group represented by the Formula e and f.

4. The compound of claim 2, wherein A is phenyl optionally substituted with lower alkyl, halogen, haloalkyl, alkoxy, cyano, nitro, —SO₂R', —NR'SO₂R", —SO₂NR'R",—COR', and —NR'R", and R' and R" are each independently hydrogen or lower alkyl.

5. The compound of claim 4, wherein G² is a group represented by the Formula c.

6. The compound of claim 5, wherein R¹ is hydrogen, lower alkyl, halo, alkoxy, cyano, SO2R', or COR', and NR'R", and R' and R" are each independently hydrogen or lower alkyl.

7. The compound of claim 5, wherein R¹ is phenyl, which is optionally substituted with halogen, lower alkyl, cyano, nitro or alkoxy.

8. The compound of claim 5, wherein R¹ is pyridinyl which is optionally substituted with halogen, lower alkyl, cyano, nitro or alkoxy.

9. The compound of claim 5, wherein R¹ is thienyl, which is optionally substituted with halogen, lower alkyl, cyano, nitro or alkoxy.

10. The compound of claim 5, wherein R¹ and R², if adjacent, taken together with the carbons to which they are attached form an optionally substituted aromatic ring, which is optionally substituted with halogen, lower alkyl, cyano, nitro or alkoxy.

11. The compound of claim 1, wherein G2 is a group represented by the Formula e.

12. The compound of claim 11, wherein A is phenyl optionally substituted with lower alkyl, halogen, haloalkyl, alkoxy, cyano, nitro, —SO₂R', —NR'SO₂R", SO₂NR'R", —NR'R", or —COR', R¹ is selected from the group consisting of hydrogen, lower alkyl, halogen, cyano, nitro, —OR', —SO₂R', —NR'SO₂R", —COR', and —NR'R", and R' and R" are each independently hydrogen or lower alkyl.

13. The compound of claim 11, wherein A is phenyl optionally substituted lower alkyl, halogen, haloalkyl, alkoxy, cyano, nitro, —SO₂R', —NR'SO₂R", —SO₂NR'R", —NR'R", or —COR'; R' and R" are each independently hydrogen or lower alkyl; and R¹ is phenyl optionally substituted with halogen, alkyl, cyano, nitro, or alkoxy.

14. The compound of claim 1, wherein the compound is selected from the group consisting of:
4-(5-phenyl-benzofuran-2-ylmethoxycarbonylamino)-biphenyl-3-carboxylic acid;
4'-fluoro-4-(5-phenyl-benzofuran-2-ylmethoxycarbonylamino)-biphenyl-3-carboxylic acid;
4'-fluoro-4-[5-(4-fluoro-phenyl)-benzofuran-2-ylmethoxycarbonylamino]-biphenyl-3-carboxylic acid;

2-(5-phenyl-benzofuran-2-ylmethoxycarbonylamino)-naphthalene-1-carboxylic acid;

2-[5-(4-fluoro-phenyl)-benzofuran-2-ylmethoxycarbonylamino]-5-isopropoxy-benzoic acid;

2-[5-(4-fluoro-phenyl)-benzofuran-2-ylmethoxycarbonyla-mino]-6-methyl-benzoic acid;

2-[5-(4-fluoro-phenyl)-benzofuran-2-ylmethoxy-carbonylamino]-5-pyridin-3-yl-benzoic acid;

5-methanesulfonyl-2-(5-phenyl-benzofuran-2-ylmethoxycarbonylamino)-benzoic acid;

4-[5-(4-fluoro-phenyl)-benzofuran-2-ylmethoxycarbonylamino]-biphenyl-3-carboxylic acid;

2-(5-phenyl-benzofuran-2-ylmethoxycarbonylamino)-5-thiophen-3-yl-benzoic acid;

5-bromo-2-(5-phenyl-benzofuran-2-ylmethoxycarbonylamino)-benzoic acid;

[3-(1H-tetrazol-5-yl)-biphenyl-4-yl]-carbamic acid 5-phenyl-benzofuran-2-ylmethyl ester;

[2-(1H-tetrazol-5-yl)-phenyl]-carbamic acid 5-phenyl-benzofuran-2-ylmethyl ester;

2-chloro-6-[5-(4-fluoro-phe-nyl)-benzofuran-2-ylmethoxycarbonylamino]-benzoic acid;

2-[5-(4-fluoro-phenyl)-benzofuran-2-ylmethoxycarbonylamino]-naphthalene-1-carboxylic acid;

2-[5-(4-fluoro-phenyl)-benzofuran-2-ylmethoxycarbonylami-no]-5-methanesulfonylamino-benzoic acid; and

[2-(5-phenyl-benzofuran-2-ylmetho-xycarbonylamino)-phenyl]-acetic acid.

15. A process for preparing a compound as claimed in claim 1, which process comprises:

esterification of the compounds having a general Formula 2 or 3:

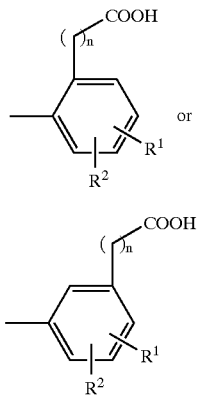

wherein $R^1$ and $R^2$ are as defined in claim 1, acylation with phosgene, followed by reaction with a compound of general Formula 2

wherein $G^1$ is as defined in claim 1, and hydrolysis, to provide a compound of the general Formula Ia or Ib

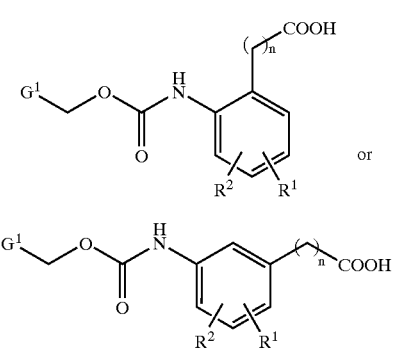

wherein n, $G^1$, $R^1$, and $R^2$ are as defined in claim 1.

16. A process for preparing a compound as claimed in claim 1, which process comprises:

acylation with phosgene of a compound of general Formula cm or co,

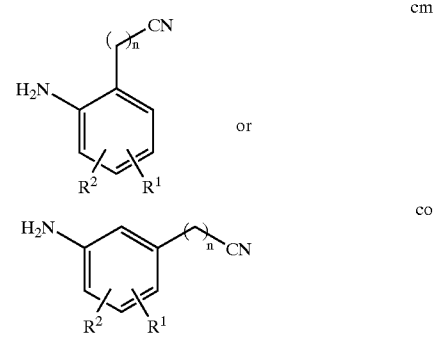

followed by reaction with a compound of general formula 2

wherein $G^1$ is as defined herein, and treatment with azide to provide a compound of general Formula Ic

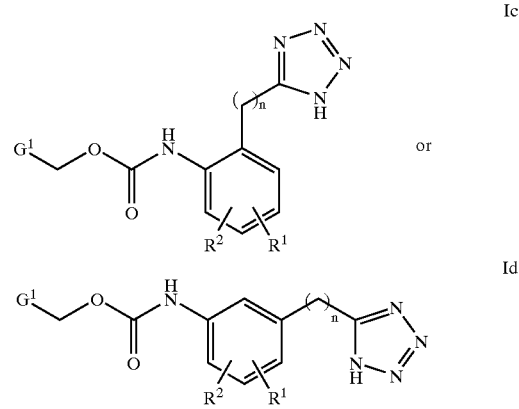

wherein n, $G^1$, $R^1$, and $R^2$ are as defined herein.

17. A pharmaceutical composition comprising a therapeutically effective amount of a compound of claim 1 in admixture with at last one pharmaceutically acceptable carrier.

18. A method of treating a subject with a disease state that is alleviated with an IP antagonist, said disease state selected from asthma and disorders of the urinary tract, said method comprising administering to a subject in need thereof an effective amount of one of more compounds of claim 1.

19. The method of treatment of claim 18, wherein the disease state comprises bladder disorders associated with bladder outlet obstruction and urinary incontinence conditions.

20. The method of treatment of claim 18, wherein the disease state comprises asthma.

* * * * *